(12) United States Patent
Klefenz

(10) Patent No.: US 7,797,051 B2
(45) Date of Patent: Sep. 14, 2010

(54) METHOD, DEVICE AND COMPUTER PROGRAM FOR GENERATING A CONTROL SIGNAL FOR A COCHLEAR IMPLANT, BASED ON AN AUDIO SIGNAL

(75) Inventor: Frank Klefenz, Mannheim (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 242 days.

(21) Appl. No.: 12/278,596

(22) PCT Filed: Feb. 1, 2007

(86) PCT No.: PCT/EP2007/000878

§ 371 (c)(1),
(2), (4) Date: Aug. 15, 2008

(87) PCT Pub. No.: WO2007/090563

PCT Pub. Date: Aug. 16, 2007

(65) Prior Publication Data

US 2009/0030486 A1  Jan. 29, 2009

(30) Foreign Application Priority Data

Feb. 10, 2006  (DE) ................ 10 2006 006 296

(51) Int. Cl.
*A61N 1/00* (2006.01)
(52) U.S. Cl. ........................................ 607/57
(58) Field of Classification Search .......... 607/57, 607/55, 137, 56; 600/559
See application file for complete search history.

(56) References Cited

U.S. PATENT DOCUMENTS

| 4,980,918 | A | 12/1990 | Bahl et al. |
| 5,381,512 | A | 1/1995 | Holton et al. |
| 5,388,182 | A | 2/1995 | Benedetto et al. |
| 7,636,603 | B1 * | 12/2009 | Overstreet et al. ............ 607/57 |
| 2005/0069162 | A1 | 3/2005 | Haykin et al. |
| 2005/0234366 | A1 | 10/2005 | Heinz et al. |

FOREIGN PATENT DOCUMENTS

WO    01/99470 A1    12/2001

OTHER PUBLICATIONS

Official communication issued in counterpart International Application No. PCT/EP2007/000878, mailed on Apr. 26, 2007.
Greenberg et al.: "A Space-Time Theory of Pitch and Timbre Based on Cortical Expansion of The Cochlear Traveling Wave Delay," Proceedings of the XLth International Symp. om Hearing; 1997; 7 pages.
Mass: "Computing With Spiking Neurons." Pulsed Neuro Networks; 1998; pp. 35-42.

* cited by examiner

*Primary Examiner*—George Manuel
*Assistant Examiner*—Robert N Wieland
(74) *Attorney, Agent, or Firm*—Keating & Bennett, LLP

(57) ABSTRACT

A method of generating a control signal for a cochlear implant based on an audio signal includes calculating first information on an activity pattern over time at a plurality of inner hair cells of an auditory model, which results based on the audio signal, and filtering out activity events described by the first information, based on a recognition of a characteristic pattern in the activity pattern, whereby cleared information is obtained. The cleared information is further used as a control signal for the cochlear implant, or the control signal for the cochlear implant is derived from the cleared information.

41 Claims, 21 Drawing Sheets

The training patterns

Nine sinuses of different frequencies

METHOD, DEVICE AND COMPUTER PROGRAM FOR GENERATING A CONTROL SIGNAL FOR A COCHLEAR IMPLANT, BASED ON AN AUDIO SIGNAL

BACKGROUND OF THE INVENTION

The present invention generally relates to a method, a device and a computer program for generating a control signal for a cochlear implant based on an audio signal, in particular, to a concept for selective generation of electrical stimuli for cochlear implants by means of a two-stage back-filtration of a neurotransmitter vesicle release distribution.

For a long time, it has been a goal in medicine and medical technologies in particular to enable people suffering from a hearing disorder to take part in normal social life with as little impairments as possible. Conventional hearing aids amplifying a received acoustic signal, and, thus, enabling patients hard of hearing to perceive acoustic signals of low loudness have already been in existence for many years.

For some years, it has been even possible to help patients with a serious and non-recoverable damage to the inner ear at least to a limited auditory sensation. For this purpose, the patient's intact auditory nerves are excited by means of electrodes of a cochlear implant. In this context, the corresponding excitation signals are derived from an audio signal which is to be returned to the patient concerned.

Furthermore, a neurophysiologically-parametrized auditory computer simulation model is known, which is described, for example, in the publication "Neuronale Repräsentation des Hörvorgangs als Basis" (Neuronal Representation of the Auditory Process as a Basis) by G. Szepannek, F. Klefenz and C. Weihs (Informatik-Spektrum, vol. 28, no. 5, pp. 389-395, October 2005, Springer).

A hydromechanical liquid column excitation in the cochlea and a traveling wave motion on the basilar membrane are modeled by a set of coupled electromechanical differential equations. Detailed explanations concerning this topic may be found, for example, in the PhD thesis "Ein psychophysiologisches Gehörmodell zur Nachbildung von Wahrnehmungsschwellen für die Audiocodierung" (A Psychophysiological Auditory Model for Replication of Perception Thresholds for Audio Coding) by F. Baumgarte (PhD thesis at the University of Hannover, 2000).

The motion, or traveling wave motion, of the basilar membrane leads to a coupling motion of the stereocilia of the inner hair cells. A deflection of the stereocilia from their rest position depolarizes a rest membrane voltage of the inner hair cell, whereby a probability of an exit of a neurotransmitter vesicle from the hair cell into the synaptic cleft is increased. Exit times of the neurotransmitter vesicles are modeled according to a model by Meddis-Poveda. Modeling the voltage shape in nerve cells is based on a work by Hodgkin and Huxley. In this context, membrane voltage is influenced by ion exchange as well as an external current through the released neurotransmitters. If a vesicle diffuses from the presynaptic inner hair cell (IHC) into a synaptic cleft, it will bond to a receptor protein of the post-synaptic membrane and release charge. By the molecules of a vesicle, the postsynaptic potential increases approximately by 0.5 to 1 mV. If the polarization of the postsynaptic nerve cell exceeds a particular threshold value v, an action potential is released.

Action potentials are characterized by their almost approximately identical course. Initially, the membrane voltage extremely strongly depolarizes for a very short duration of less than 1 ms, subsequently, it hyperpolarizes and is blocked for a period of time in which no further action potentials can occur.

SUMMARY

According to an embodiment, a method of generating a control signal for a cochlear implant, based on an audio signal, may have the steps of: calculating first information describing an activity pattern over time at a plurality of inner hair cells of an auditory model, which is yielded based on the audio signal; filtering out activity events described by the first information based on a recognition of a characteristic pattern in the activity pattern, for achieving, from the first information, cleared information by eliminating activity events pertaining to a characteristic pattern or by eliminating activity events not pertaining to a characteristic pattern, wherein the recognition of a characteristic pattern includes recognizing a line-shaped curve in a representation of the activity pattern over time and over an index of the inner hair cells as a characteristic pattern; and using the cleared information as a control signal for a cochlear implant, or deriving a control signal for a cochlear implant from the cleared information.

An embodiment may have: a computer program for performing a method of generating a control signal for a cochlear implant, based on an audio signal, wherein the method may have the steps of: calculating first information describing an activity pattern over time at a plurality of inner hair cells of an auditory model, which is yielded based on the audio signal; filtering out activity events described by the first information based on a recognition of a characteristic pattern in the activity pattern, for achieving, from the first information, cleared information by eliminating activity events pertaining to a characteristic pattern or by eliminating activity events not pertaining to a characteristic pattern, wherein the recognition of a characteristic pattern includes recognizing a line-shaped curve in a representation of the activity pattern over time and over an index of the inner hair cells as a characteristic pattern; and using the cleared information as a control signal for a cochlear implant, or deriving a control signal for a cochlear implant from the cleared information, when the computer program runs on a computer.

According to another embodiment, a device for generating a control signal for a cochlear implant based on an audio signal may have: a calculator for calculating a first information on an activity pattern over time at a plurality of inner hair cells of an auditory model, which is yielded due to the audio signal; a filter for filtering out activity events described by the first information based on a recognition of a characteristic pattern in the activity pattern in order to achieve, from the first information, cleared information, by eliminating activity events pertaining to a characteristic pattern, or by eliminating activity events not pertaining to a characteristic pattern, wherein the recognition of a characteristic pattern includes recognizing a line-shaped curve in a representation of the activity pattern over time and over an index of the inner hair cells as a characteristic pattern; and a controller for controlling the cochlear implant, which is configured to use the cleared information or information derived from the cleared information as a control signal for the cochlear implant.

The present invention provides a method for generating a control signal for a cochlear implant, based on an audio signal. The inventive method includes calculating a first information about an activity pattern over time at a plurality of inner hair cells of an auditory model which results due to the audio signal, as well as filtering out activity events described by the first information, based on a recognition of a characteristic pattern in the activity pattern. By the filtering out, cleared information is obtained. The cleared information is further used as a control signal for the cochlear implant, or the control signal is derived from the cleared information.

The present invention is based on the knowledge that in an activity pattern, a multitude of activity impulses is present at a plurality of inner hair cells of an auditory model over time, which are not relevant for a patient's auditory sensation. Thus, the central idea of the present invention is to recognize a characteristic pattern in the nerve activity pattern and to decide, based on the recognition of the characteristic pattern, which activity events are to be filtered out because they are only of secondary importance for a patient's perception, for example. Further, it has been realized that there is a plurality of characteristic patterns giving a cue whether particular activity events are to be filtered out or not. For example, if two activity events occur at the same inner hair cell temporally shortly one after the other, then only the first occurrence will contribute to an auditory sensation. Furthermore, characteristic trajectories (line-shaped patterns) occur in the activity pattern. Depending on the case of application, it may be advantageous in this context, for example, to filter out, or to remove, either activity events belonging to a trajectory or activity events not belonging to a trajectory. However, in summary, it may be established that according to central idea of the present invention, activity events to be filtered out may be respectively recognized by identifying characteristic patterns.

By the filtering out, cleared information develops. It has been shown that an improved auditory sensation may be achieved in a patient if cleared information, in which superfluous activity events are removed, is used as a control signal for the cochlear implant or as an initial basis for deriving the control signal of the cochlear implant.

Within the framework of the present invention, it has been further realized that it is particularly the activity pattern over time at a plurality of inner hair cells of an auditory model that is particularly suitable for filtration so as to filter out interfering information not relevant for intelligibility of speech, for example, based on a recognition of a characteristic pattern.

It has been found that especially in the activity pattern at a plurality of inner hair cells, speech signals result in characteristic signal waveforms or patterns enabling discrimination between speech signals and interfering ambient noise. When establishing which activity events are to be filtered out from the activity pattern over time at the plurality of inner hair cells, neurophysiological findings, for example, may be utilized, giving information which activity patterns in a neuronal network replicating the human brain, for example, yield a particular strong response.

Then, for example, activity events are filtered out from the first information, which are recognized, due to a characteristic pattern occurring in the activity pattern, as leading only to a weak reaction in the human brain. It has been found that the human brain particularly strongly responds to particular characteristic patterns, while it only shows a negligible reaction upon the occurrence of other characteristic patterns in the activity pattern. A determination of the characteristic patterns to which the human brain sensitively reacts may be determined by observing cerebral currents, or observing cerebral activities, for example.

It should be understood that it has been shown, for example, that activity events in the activity pattern occurring subsequently to the release of an action potential at a synapse, or a nerve fiber, within a refractory period (dead period) of the synapse, or the nerve fiber, are not relevant for intelligibility of speech. Furthermore, it is those activity events which do not belong to a trajectory in the activity pattern over time at the plurality of inner hair cells that are not relevant for intelligibility of speech.

Thus, the present invention allows eliminating, from the activity pattern over time at the plurality of inner hair cells, the information which is not of significant importance for a patient with a cochlear implant, or even has an interfering effect for such a patient. Thus, the auditory sensation of the patient concerned may be improved.

Further, the present invention has the advantage that less activity events occur in the control signal for the cochlear implant than when using conventional concepts. This facilitates the provision of the nerve stimulation signals generated by the cochlear implant based on the control signal. Typical cochlear implants are only able to issue a particular number of nerve stimulation impulses per unit of time, wherein the circuit complexity increases the more nerve stimulation impulses have to be issued per unit of time. Energy consumption increases approximately linearly to a number of nerve stimulation impulses issued. Thus, the complexity of the cochlear implant as well as its power consumption decrease by the inventive concept of filtering out "unnecessitated" activity impulses, or activity impulses not relevant for intelligibility of speech, from the activity pattern.

In a further embodiment, the first information on the activity pattern over time describes temporal devolutions of a number of released neurotransmitter vesicles for a plurality of inner hair cells. In this embodiment, the filtering out includes removing, from the first information, neurotransmitter vesicle occurrences not contributing to a generation of an action potential or not generating an action potential. It has been shown that neurotransmitter vesicle occurrences are only of importance for the cochlear implant, or a human patient, if the corresponding neurotransmitter vesicle occurrences actually result in an action potential. A correspondingly cleared information describing only the neurotransmitter vesicle occurrences which do result in an action potential comprises a significantly lower amount of data than the associated uncleared information describing all neurotransmitter vesicle occurrences. Thus, generating the cleared information about a neurotransmitter vesicle occurrence represents a possibility of decreasing the amount of data in a system for operating a cochlear implant. For example, the cleared information mentioned may be exchanged significantly more efficient with respect to resources than an uncleared information about the neurotransmitter vesicle occurrence. This is of particular importance if the cleared information about the neurotransmitter vesicle occurrence is exchanged between several components of a system for operating a cochlear implant.

In many cases, for example, the (conventionally uncleared) information about a neurotransmitter vesicle occurrence is transmitted wireless or on-wire between an external processing and the cochlear implant, wherein the capacity of the corresponding transmission path has to be adapted to the amount of data. In this context, a decrease of the amount of data due to the inventive clearing of the information (filtering out) directly causes less resources (e.g. frequency resources or energy) to be needed to enable the corresponding transmission.

Furthermore, when using the present invention, each further processing unit has to process only a smaller amount of data (only the cleared information about the neurotransmitter vesicle occurrence) than is usually conventional (uncleared information about the neurotransmitter vesicle occurrence). By the inventive reduction of the amount of data due to filtering out, or removing, neurotransmitter vesicle occurrences not contributing to a generation of an action potential or not generating an action potential, no information significant for a patient is lost. Thus, the amount of data and the need for resources necessitated for the processing may be significantly decreased in a quasi loss-free way.

Advantageously, the activity pattern includes temporal devolutions of a number of neurotransmitter vesicles released per unit of time or a number of neurotransmitter vesicles present in the synaptic cleft during a particular time interval or at a particular point in time. However, the activity pattern may also only include information as to whether neurotransmitter vesicles are released in the synaptic cleft during a particular time interval or as to whether neurotransmitter vesicles are present in the synaptic cleft during a particular time interval or at a particular point in time.

The fact whether a neurotransmitter vesicle occurrence contributes to a generation of an action potential or not, or whether a neurotransmitter vesicle occurrence generates an action potential or not, may be determined, for example, by help of a model for a generation of action potentials. The corresponding model may provide an estimation, for example, as to whether a neurotransmitter vesicle occurrence contributes to a generation of an action potential or generates an action potential. For example, if, according to the corresponding model, multiple neurotransmitter vesicles are necessitated to generate an action potential, then it is possible, for example, to remove all those neurotransmitter vesicle occurrences which are only preparatory necessitated for triggering an action potential, so that the cleared information only contains an information about the occurrence of the last neurotransmitter vesicle which eventually triggers the action potential.

In a further embodiment, it is advantageous to remove, during the filtering out, neurotransmitter vesicle occurrences for hair cells the synapses of which are in a refractory period, or in a dead period, due to a release of an action potential. Specifically within an absolute dead time, or an absolute refractory period, it may be assumed that a neurotransmitter vesicle occurrence on no account contributes to the release of an action potential. Thus, taking into consideration a refractory period of synapses represents a criterion particularly easy to evaluate, with reference to which non-relevant neurotransmitter vesicle occurrences may be removed from the first information on the activity pattern.

The occurrence of activity events within the refractory period is recognizable within the framework of a pattern recognition by the presence of at least two activity events at short time intervals at the same inner hair cell.

In a further embodiment of the present invention, the filtering out of the activity events based on a characteristic pattern in the activity pattern includes determining which of the activity events described by the first information belong to a trajectory, or do not belong to a trajectory. In this case, the filtering out includes deriving the cleared information on the activity pattern, wherein the cleared information is formed from the first information by eliminating activity events which do not belong to a trajectory.

The corresponding embodiment is based on the crucial knowledge that activity events are particularly important for intelligibility of speech if the activity events on different auditory nerves are in a temporal interrelation, which may be described by a trajectory. It has been shown that particularly with speech signals, traveling waves occur on the basilar membrane which excite different hair cells temporally one after the other and in a characteristic temporal sequence determined by a propagation speed on the basilar membrane. Further, it has been shown that by its construction as a neuronal network, the human brain particularly strongly responds to a corresponding trajectory, or a predetermined characteristic sequence of activity events. Thus, the activity events belonging to a trajectory are particularly relevant for intelligibility of speech. In contrast, the activity events not lying on a trajectory are less relevant, or even interfering, for intelligibility of speech. Thus, by the inventive elimination of activity events which do not belong to a trajectory, not only the amount of data necessitated for describing the activity events is decreased, but at the same time, also the intelligibility of speech of the speech information contained in the audio signal is improved for a patient with a cochlear implant.

However, in an alternative embodiment, it also possible to filter out, or eliminate, activity events which lie on a trajectory from the first information. Namely, interference noises comprising a characteristic trajectory exist. For example, click impulses frequently occurring by transmission interferences result in a traveling wave on the basilar membrane, which is recognizable as a characteristic trajectory in the activity pattern. Thus, filtering out activity events lying on a trajectory allows a decrease, or elimination, of interferences, and thus results in an improved auditory sensation.

In an embodiment, the first information describes temporal devolutions of a number of released neurotransmitter vesicles for a plurality of inner hair cells, wherein each hair cell of the plurality of inner hair cells is allocated to a temporal devolution. The number of released neurotransmitter vesicles may include, for example, a number of newly released neurotransmitter vesicles for individual periods of time. However, the temporal devolutions may also describe a total number of neurotransmitter vesicles present at the synaptic cleft. It has been shown that trajectories are recognizable in the number of released neurotransmitter vesicles, comprising a characteristic form in the case, for example, of a speech signal being contained in the audio signal. In other words, in the temporal devolution of the neurotransmitter vesicle release across a plurality of nerve cells, characteristic line-shaped patterns (trajectories) are recognizable, wherein the activity events belonging to the trajectories provide a particularly large contribution to intelligibility of speech of the speech signal described by the neurotransmitter vesicle occurrence.

In a further embodiment, the first information describes a plurality of temporal voltage shapes at a plurality of nerve fibers coupled to different inner hair cells. Here, each hair cell is allocated to a temporal voltage shape at an associated nerve fiber. It has been realized that, similar to the neurotransmitter vesicle occurrence, in the voltage shapes at a plurality of nerve fibers coupled to different hair cells (shortly referred to as nerve activity pattern), too, line-shaped characteristic nerve fiber-spanning structures (trajectories) are recognizable, which include information on a speech signal contained in the audio signal. Further, it has been realized that by removing action potentials, or activity events, which do not belong to one of the trajectories from the temporal voltage shapes at the plurality of nerve fibers, intelligibility of speech may be improved. Further, interferences may be decreased if activity events belonging to particular (interfering) trajectories are removed.

In a further embodiment, determining which of the activity events described by the first information do not belong to a trajectory includes performing a pattern recognition. Performing the pattern recognition includes receiving the information on the activity pattern over time as well as interpreting the activity pattern over time for the plurality of hair cells as a two-dimensional representation. A first direction of the two-dimensional representation describes the time, while, in contrast, a second direction of the two-dimensional representation describes an index of the inner hair cells. Information contained in the two-dimensional representation describes the occurrence of activity impulses in dependence on the time and the index of the inner hair cells. Performing the pattern recognition further includes identifying a curve shape in the two-dimensional representation as a trajectory, if, with regard to a pregiven similarity measure, the curve shape comprises at least one pregiven similarity to a comparison curve shape.

It has been realized that trajectories may be identified in an advantageous manner by performing a pattern recognition based on the first information. If the first information is represented two-dimensionally in the manner described, line-shaped curves (trajectories) occur in the two-dimensional representation, wherein a trajectory is thus a line-shaped curve linking activity events in different inner hair cells if the activity events are represented two-dimensionally over time and over the one index of the inner hair cells.

In other words, a pattern recognition may be advantageously employed to recognize, in a two-dimensional representation of the activity events over time and over an index of the inner hair cells, that information which is relevant, or not relevant, for intelligibility of speech, for example.

In a further embodiment, determining which activity impulses do not belong to a trajectory includes determining activity impulses belonging to a trajectory. In one embodiment, a trajectory is only recognized if a number of activity impulses belonging to a trajectory is larger than a pregiven minimum number. In other words, only trajectories with a pregiven minimum length are recognized. Shorter trajectories, in contrast, are not taken into consideration. Corresponding methods yield a further reduction of an amount of data since only long trajectories (longer than the pregiven minimum number) are recognized. In contrast, short trajectories are not identified as trajectories, whereby, for example, activity events belonging to a short trajectory are removed from the first information. Thus, not only the amount of information is reduced, but, in turn, intelligibility of speech is significantly increased. Further, the other way round, especially those activity events belonging to a particularly long trajectory (longer than a pregiven minimum length) may be removed, since particularly long trajectories may describe, for example, a wide-band interference (e.g. a click).

In an embodiment, identifying a curve shape in the two-dimensional representation includes comparing the two-dimensional representation or a portion of the two-dimensional representation with a comparison curve shape. It has been realized that trajectories may be described by a limited number of comparison curve shapes. A comparison with a comparison curve shape may be realized in a resource-efficient manner. Advantageously, plural comparison curve shapes describing plural possible trajectories are used. Using comparison curve shapes is particularly simple since trajectories typically represent straight or curved lines, wherein the trajectories to be recognized typically do not change the direction of curvature. In other words, across an entire course, trajectories are typically either curved to the right or curved to the left or straight. However, line-shaped curves with a single direction of curvature may be at least approximately described by a very limited number of comparison patterns. Thus, a pattern comparison is an efficient procedure for identifying a trajectory in the two-dimensional representation.

Advantageously, straight or hyperbola-curved curves are used as comparison patterns. It has been realized that due to the nature of the cochlea, trajectories typically comprise a corresponding form. It is substantially the propagation speed of traveling waves on the basilar membrane of the cochlea that is responsible for the curvature of the trajectories.

In a further embodiment, identifying a curve shape in the two-dimensional representation as a trajectory includes a step distortion of the two-dimensional representation to obtain a distorted two-dimensional representation of the activity pattern over time. Identifying a curve shape as a trajectory further includes determining whether an approximately straight line is contained in the distorted two-dimensional representation, wherein an approximately straight line in the distorted two-dimensional representation is identified as a trajectory. The corresponding concept is based on the knowledge that trajectories may be bent to a straight, or approximately straight, line by a suitable distortion of the two-dimensional representation. However, a recognition of an approximately straight line is possible in a particularly simple manner, since a straight, or approximately straight, line is recognizable by the simultaneous occurrence of a plurality of activity events in a single row of the distorted two-dimensional representation. However, recognition of the simultaneous occurrence of a plurality of activity events in a row of the two-dimensional representation may be easily recognized by a summation of the activity events occurring in the corresponding row and by comparing the sum value to a threshold value.

Thus, a step distortion represents a particularly efficient method of a pattern recognition for a bent, or curved, line, wherein the actual pattern recognition is only designed to detect an occurrence of a straight, or approximately straight, line.

In a further embodiment, deriving the cleared information includes recognizing a trajectory in the first information, marking activity events belonging to the trajectory, as well as eliminating non-marked activity events. Thus, all those activity events are removed from the first information that are not marked as belonging to a trajectory. Here, initially a recognition of trajectories over a portion of the first information may be performed, whereupon non-marked events are deleted. The corresponding procedure may be implemented in a more resource-efficient manner than a generation of new cleared information, which could be made, for example, by taking over the activity events belonging to the trajectories. If the activity events which do not belong to a trajectory are removed from the first information, it is not essential to compile a copy of the first information.

In a further embodiment, calculating the first information on the activity pattern over time includes calculating the activity pattern over time at a plurality of inner hair cells of an auditory model, wherein the inner hair cells are arranged at different location along the cochlea. Thus, the different hair cells comprise sensitivity peaks at different frequencies. Thus, a frequency selectivity of the activity events at the different hair cells results. Thus, the activity pattern over time is particularly characteristic for a range of frequencies relevant for intelligibility of speech, for example. Events in the audio signal with a wide-band frequency spectrum, such as beginnings of vocals or consonants, are thus reflected in the trajectories in a particularly characteristic manner.

In other words, the different inner hair cells are advantageously selected such that they comprise a peak sensitivity at different frequencies contained in the audio signal.

The present invention further includes a computer program for performing the inventive method described.

The present invention further includes a device for generating a control signal for a cochlear implant based on an audio signal. The inventive device includes means designed to perform the steps described with regard to the method.

BRIEF DESCRIPTION OF THE DRAWINGS

Embodiments of the present invention will be detailed subsequently referring to the appended drawings, in which.

DETAILED DESCRIPTION OF THE INVENTION

Figure 1:
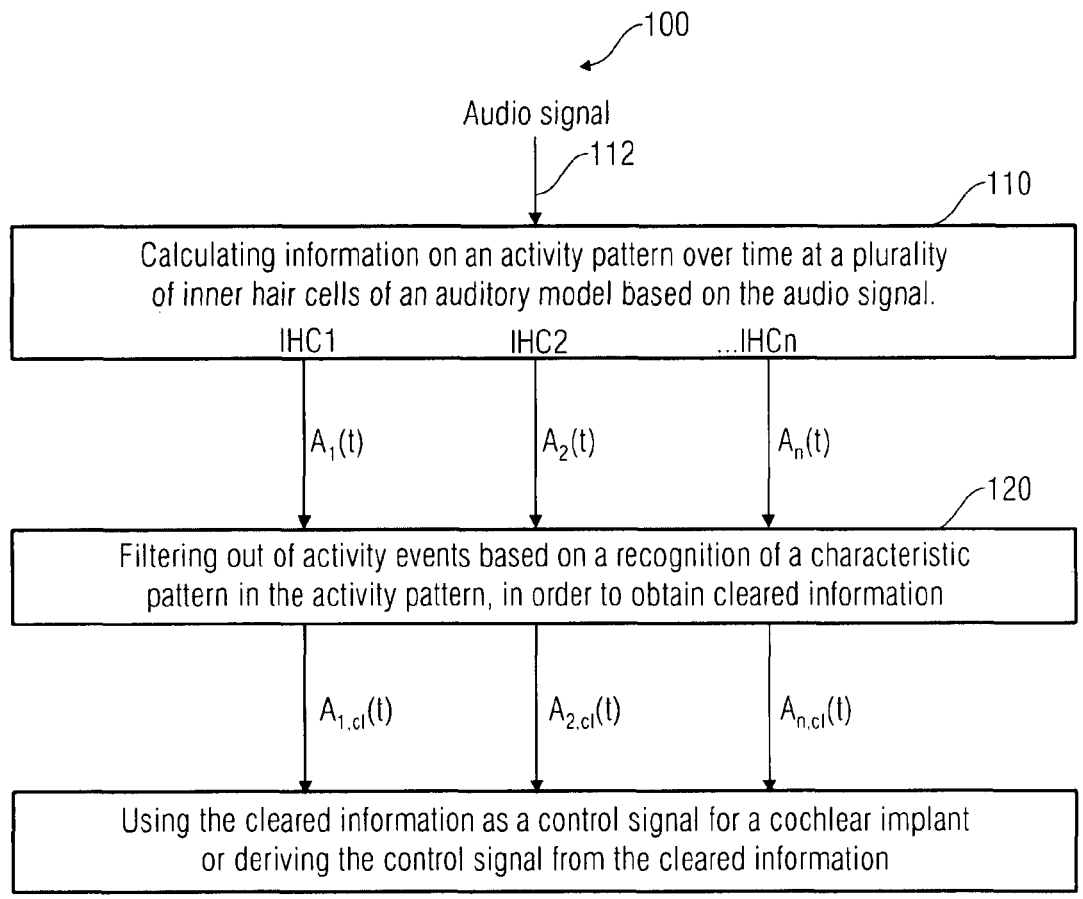
FIG. 1 is a flow diagram of an inventive method for generating a control signal for a cochlear implant based on an audio signal, according to a first embodiment of the present invention.

FIG. 1 shows a flow diagram of an inventive method for generating a control signal for a cochlear implant, according to a first embodiment of the present invention. In its entirety, the flow diagram of FIG. 1 is designated 100.

In a first step 110, the inventive method includes calculating information on an activity pattern over time at a plurality of inner hair cells of an auditory model due to the audio signal 112. Thus, an activity pattern at a plurality of inner hair cells is known, wherein the inner hair cells are designated IHC1, IHC2 to IHCn. In other words, respectively associated temporal devolutions are known for the plurality of inner hair cells IHC1 to IHCn. Here, a temporal devolution belonging to a particular inner hair cell IHCi typically includes one or plural activity events, wherein the activity events describe an activity at the associated inner hair cell IHCi.

For example, an activity event may describe an occurrence of an excitation of the respective inner hair cell IHCi, e.g. a deflection of a stereocilium belonging to the inner hair cell IHCi, a change, or a maximum or a minimum, in a calcium concentration in the inner hair cell IHCi, a change, a minimum or a maximum in a transmitter release rate in the inner hair cell IHCi, a neurotransmitter vesicle occurrence in the inner hair cell or an action potential generated by the inner hair cell IHCi.

In other words, a temporal devolution belonging to an inner hair cell IHCi indicates an activity event by a local minimum or a local maximum occurring in the temporal devolution, for example, or by a pregiven threshold value being exceeded or being fallen below by one of the mentioned quantities.

Further, it should be understood that an activity event is typically based on the excitation of the corresponding inner hair cell by a motion of the basilar membrane.

Thus, the information on an activity pattern over time at the plurality of inner hair cells of the auditory model includes a description of a plurality of temporal devolutions $A_1(t), A_2(t), A_n(t)$, wherein the individual temporal devolutions separately describe the excitation of the associated inner hair cells.

Based on the information on the activity pattern, or based on the individual temporal devolutions $A_1(t), A_2(t)$ to a $A_n(t)$, a second step 120 of the inventive method 100 includes filtering out activity events based on a recognition of a characteristic pattern in the activity pattern, so as to obtain cleared information. Here, advantageously activity events having only a secondary importance for the intelligibility of speech of a speech signal described by the activity pattern are filtered out from the activity pattern.

Filtering out the activity events may be made either separately for each single one of the temporal devolutions $A_1(t)$, $A_2(t)$ to $A_n(t)$, or a common filtering out may be performed, wherein at least two of the temporal devolutions $A1(t), A2(t)$ to An(t) are respectively utilized for the filtering out. Thus, cleared temporal devolutions $A_{1,cl}(t), A_{2,cl}(t)$ to $A_{n,cl}(t)$ result by filtering out, wherein each cleared temporal devolution $A_{i,cl}(t)$ is allocated to a corresponding associated temporal devolution $A_i(t)$. Here, a cleared temporal devolution $A_{i,cl}(t)$ contains the activity events which are contained in the associated uncleared devolution $A_i(t)$ and which are relevant for intelligibility of speech, for example.

In other words, it is examined whether a characteristic pattern is contained in the activity pattern. Based on a recognized characteristic pattern formed by a plurality of activity events, activity events which do not belong to the recognized pattern are identified and are filtered out (or eliminated) from the uncleared information on the activity pattern. Alternatively, however, also activity events which are part of a recognized characteristic pattern may be filtered out from the uncleared information. In this context, not all activity events belonging to the characteristic pattern have necessarily to be filtered out, although filtering out all activity events belonging to the characteristic pattern represents an option. Rather, it may be sufficient, for example, to recognize a particular characteristic pattern in the uncleared activity pattern, and then to filter out activity impulses forming a real part (in the sense of a real subset) of the characteristic pattern.

Thus, in the cleared temporal devolution of $A_{i,cl}(t)$, activity events, for example, which are contained in the uncleared temporal devolution $A_i(t)$ but which are not relevant for intelligibility of speech are filtered out, or removed.

The cleared temporal devolutions $A_{1,cl}(t), A_{2,cl}(t)$ to $A_{n,cl}(t)$ thus form cleared information from which activity events not relevant for intelligibility of speech are removed, compared to the uncleared information (described by $A_1(t), A_2(t)$ to $A_n(t)$).

Further, a temporal relation of activity events which are considered relevant for intelligibility of speech (that is, which are not filtered out) is not changed, in the cleared information, with respect to the uncleared information. In other words, those activity events considered relevant for intelligibility of speech remain unchanged in the cleared information, at least in terms of time, but also in terms of amplitude, if necessitated.

Method 100 further includes using the cleared information as a control signal for a cochlear implant or deriving the control signal from the cleared information. In other words, a control signal supplied to a cochlear implant is derived from the cleared information describing, or including, cleared temporal devolutions $A_{1,cl}(t), A_{2,cl}(t)$ to $A_{n,cl}(t)$. Thus, based on the activity events described by the temporal devolutions $A_{1,cl}(t), A_{2,cl}(t)$ to $A_{n,cl}(t)$, a signal allowing the cochlear implant to generate electric stimulation impulses for nerve fibers of the auditory nerves (spiral ganglia cells) based on this is derived.

For the case of the cleared information describing a cleared neurotransmitter vesicle occurrence at a plurality of inner hair cells, the cleared information may be used directly or in an encoded form as a control signal for a cochlear implant, for example. In a similar manner, for example, cleared information describing cleared action potentials at a plurality of auditory nerves, too, may be used directly for controlling a cochlear implant. However, deriving a control signal from the cleared information may also include a further conversion of the cleared information, so that new information suitable for controlling the cochlear implant is derived from the cleared information. The last-mentioned procedure is reasonable, for example, if the cleared information is not yet directly suitable for controlling a cochlear implant, that is, if the cleared information describes a deflection of stereocilia of inner hair cells or a concentration or a release of ions in the inner hair cell, for example.

In summary, it may thus be established that it has been realized that by filtering out activity events from an activity pattern at a plurality of inner hair cells based on a recognition of a characteristic pattern in the activity pattern, activity events which are not relevant for intelligibility of speech may be eliminated with particularly small effort and particularly good results.

The reason for this is that an excitation pattern, or an activity pattern, at, or in, a plurality of inner hair cells makes characteristics relevant for the intelligibility of speech particularly clearly recognizable over time. Here, it is established that in the external ear, the middle ear and the inner ear (cochlea), a transformation of speech signals is made in a manner such that excitation patterns, or activity patterns, at, or in, the inner hair cells comprise a characteristic structure when speech signals (or also some interference signals) are present. Thus, from the activity patterns over time at the plurality of inner hair cells, it is apparent in a simple manner which portions of the activity patterns are actually relevant for intelligibility of speech.

For example, such portions which cause a particularly strong reaction of the neuronal network when supplied as a parallel signal to a neuronal network are particularly relevant for intelligibility of speech, since a recognition of speech signals by a human is made by a network of neurons.

It has been found that activity events, for example, which do not lead to an action potential on an auditory nerve are not, or only little, relevant for intelligibility of speech. Further, it has been realized that single activity events not belonging to a group of interrelated, or correlated, activity events are not, or only little, relevant for intelligibility of speech. Vocals, consonants and sounds respectively distinguish themselves by causing a plurality of activity events at a plurality of inner hair cells of an auditory model, which on the whole describe a pattern characteristic for a vocal, a consonant or a sound. In this context, for example, it is such activity events which are caused by a traveling wave on the basilar membrane of the auditory model that are relevant for intelligibility of speech. Such traveling waves, for example, describe a beginning of a vocal and further also appear within the fine structure of the vocal. Details with respect to this will be further explained in the course of the description.

In the following, it will be described how a nerve activity pattern at a plurality of auditory nerves coupled to inner hair cells may be calculated using an auditory model, based on an audio signal. From the following explanations, it is further apparent which intermediate, or final, quantities of the calculation may be utilized for a description of the uncleared activity pattern.

Figure 2:
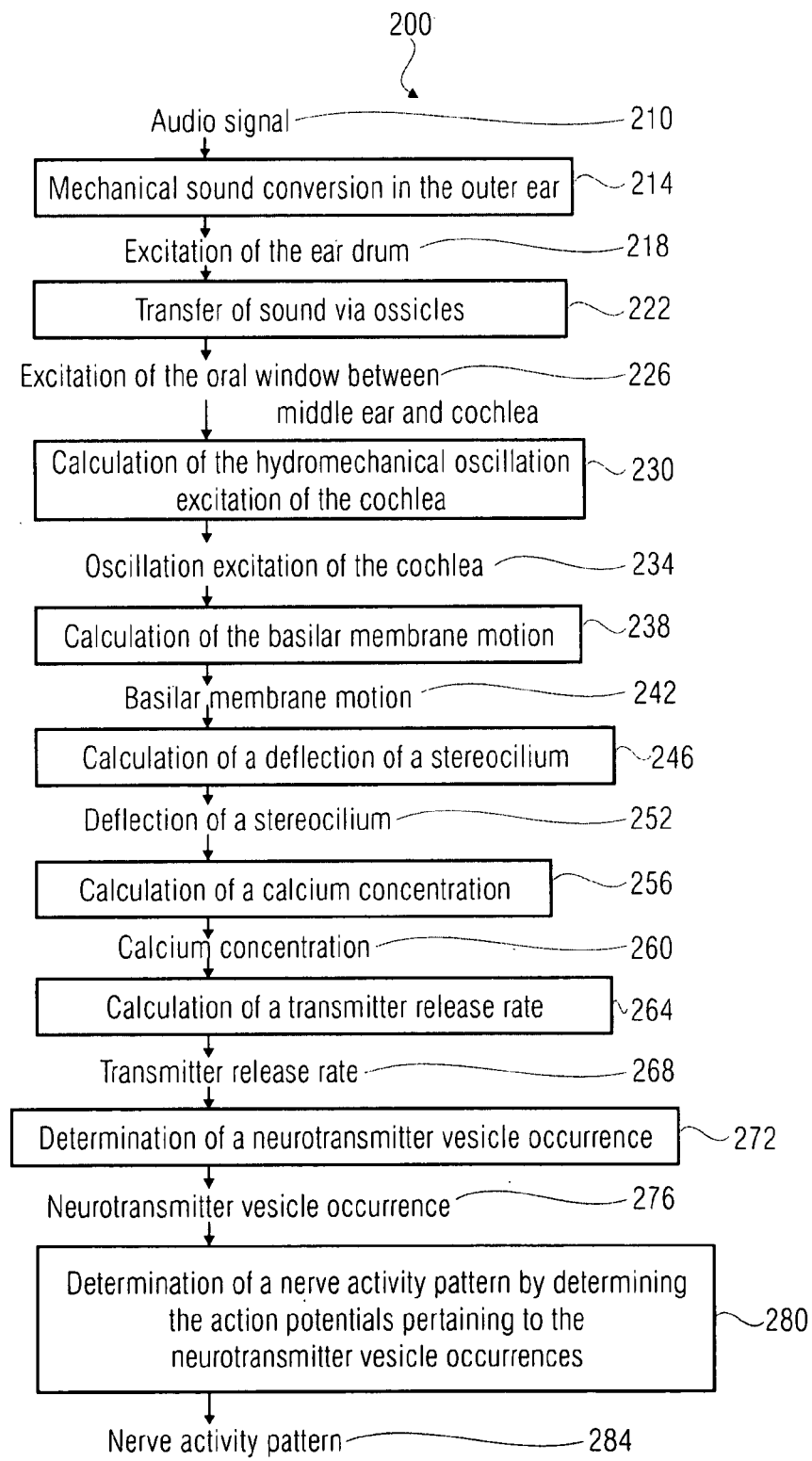
FIG. 2 is a schematic illustration of a flow in a simulation of a human auditory system as well as the intermediate and final results occurring in the simulation.

For this purpose, FIG. 2 shows a schematic illustration of the flow in a simulation of a human auditory system as well as the intermediate and final results occurring in the simulation. In its entirety, the schematic illustration of FIG. 2 is designated 200.

Thus, the schematic illustration 200 of FIG. 2 describes a simulation model of a human auditory system. An audio signal 210 serves as an input signal for the simulation model 200. Based on the audio signal 210, in a first step 214, a mechanical sound conversion in an external ear is evaluated, whereby an excitation 218 of an eardrum is ascertained. In a second step 222, a sound transmission via ossicles is calculated, or simulated, whereby an excitation 226 of an oval window between a middle ear and a cochlea is ascertained from the excitation 218 of the eardrum. In a third step 230, a hydromechanical vibration excitation 234 of the cochlea is calculated, or simulated. In a fourth step 238, a basilar membrane motion 242 is ascertained from the vibration excitation 234 of the cochlea. In a fifth step 246, a deflection 252 of a stereocilium is concluded from the basilar membrane motion 242. Based on the deflection 252 of the stereocilium, then, in a sixth step 256, a calcium concentration 260 in a hair cell is calculated. The calcium concentration 260 is then utilized to calculate, in a seventh step 264, a transmitter release rate 268 of transmitter substances. Based on the transmitter release rate 268, in an eighth step 272, a neurotransmitter vesicle occurrence 276 describing an occurrence of neurotransmitter vesicles is derived. Eventually, in a ninth step 280, a nerve activity pattern 284 is derived from the neurotransmitter vesicle occurrence 276. The nerve activity pattern 284 in this context approximately describes an activity on the nerve cells of a (human or animal) auditory nerve occurring in a healthy auditory system. The nerve activity pattern 284 is thus well suitable for providing a statement concerning stimulation of auditory nerves by a cochlear implant.

It should be understood that within the framework of the simulation model 200, several of the steps 214, 222, 230, 238, 246, 256, 264, 272, 280 may be put together without calculating a corresponding intermediate result. In other words, several steps may be processed in a simplified step without the calculation of the intermediate steps shown in the graphic illustration 200.

Thus, the deflection 252 of a stereocilium, the calcium concentration 260 in an inner hair cell, the transmitter release rate 268 in an inner hair cell, a neurotransmitter vesicle occurrence 276 in an inner hair cell or a nerve activity pattern 284 present at the inner hair cell (or the associated temporal devolution) may respectively represent an activity pattern, or part of an activity pattern, at an inner hair cell.

In other words, a temporal devolution of a deflection of a stereocilium belonging to an inner hair cell represents a temporal devolution, for example, as is designated $A_1(t)$ in the flow diagram 100. Corresponding temporal devolutions of deflections of stereocilia belonging to further inner hair cells in this example form the further uncleared temporal devolutions $A_2(t)$ to $A_n(t)$. For example, in the example just described, such deflections of the stereocilia are filtered out which do not lead to action potentials in the nerve activity pattern 284, since such deflections of the stereocilia are not relevant for intelligibility of speech.

For example, the concentrations 260 of calcium ions in a plurality of inner hair cells may equally form an activity pattern, wherein a temporal devolution of the calcium concentration 260 in the i-th inner hair cell forms the i-th temporal devolution $A_i(t)$. When considering the calcium concentration, a significant increase in the calcium concentration above a particular threshold value or a decrease in the calcium concentration below a particular threshold value, for example, is an activity event.

For example, the temporal devolutions $A_i(t)$ may also only describe a deviation of the current calcium concentrations from equilibrium calcium concentrations. In this case, an activity event is described by a significant deviation of the respective calcium concentration to the top or to the bottom. According to the present invention, when using a description of the calcium concentration as the activity pattern, in step 120, such variations in the calcium concentration which do not contribute to intelligibility of speech, or are not relevant for intelligibility of speech, are filtered out. Thus, cleared information $A_{i,cl}(t)$ results, in which the variations in the calcium concentration not relevant for intelligibility of speech are not contained anymore, or are set to zero, for example.

Further, the temporal devolution of a transmitter release rate 268 or a transmitter release probability in a plurality of inner hair cells may be used, too, as an activity pattern over time. The temporal devolutions $A_i(t)$ are formed by the transmitter release rate or transmitter release probability in the i-th inner hair cell. If it is established, for example, in the second step 120 according to the flow diagram 100, based on a recognition of a characteristic pattern in the activity pattern, that a non-diminishing transmitter release rate 268, or transmitter release probability, is not relevant for intelligibility of speech, then the transmitter release rate 268, or transmitter release probability, calculated according to FIG. 2 will be set to zero in the cleared activity pattern $A_{1,cl}(t)$ to $A_{n,cl}(t)$, for example, within the framework of the second step 120. It should be understood that when considering the transmitter release rate 268, or the transmitter release probability, the presence of a transmitter release rate greater than zero, or a transmitter release probability greater than zero, for example, may be seen as an activity event.

Further, also a neurotransmitter vesicle occurrence 276 in a plurality of inner hair cells may form an activity pattern. The temporal devolutions $A_i(t)$ are here formed by a number of released neurotransmitter vesicles, for example. In other words, in the case mentioned, a temporal devolution $A_i(t)$ describes how many neurotransmitter vesicles are present in a released form during a particular period of time, or a time interval, for example. However, the neurotransmitter vesicle occurrence 276 may also describe how many neurotransmitter vesicles are newly released during a time period, or a time interval. The corresponding temporal devolution may further describe, for example, how many neurotransmitter vesicles are released in the pre-synaptic inner hair cell per unit of time, or are on the whole present in a released form in a time interval or at a point in time. Furthermore, the neurotransmitter vesicle occurrence 276 may also describe how many neurotransmitter vesicles diffuse, per unit of time, for example, from the pre-synaptic inner hair cell into the synaptic cleft which couples the pre-synaptic inner hair cell to a nerve fiber.

In other words, by neurotransmitter vesicle occurrence, a number of neurotransmitter vesicles actually present released per unit of time is meant, wherein it is not relevant for the present invention where exactly the corresponding number of neurotransmitter vesicles or the corresponding release rate of neurotransmitter vesicles is determined within a hair cell or a synapse. It has to be assumed that neurotransmitter vesicles released in the pre-synaptic part of the inner hair cell diffuse into the synaptic cleft with a certain time constant.

It should be further understood that a neurotransmitter vesicle occurrence may be described both in terms of quality and quantity to describe an activity pattern in the sense of the present invention. In other words, a temporal devolution $A_i(t)$ belonging to a neurotransmitter vesicle occurrence 276 may describe, for example, how many neurotransmitter vesicles are released or are present in a released form. The temporal devolution $A_i(t)$ may also give only qualitative information as to whether neurotransmitter vesicles are released in a time interval, or are present in a released from.

When considering a neurotransmitter vesicle occurrence 276 in, or at, a plurality of inner hair cells of an auditory model as the activity pattern, the release of a number of neurotransmitter vesicles in a time unit greater than a particular threshold value, may also be seen as activity events, for example. For example, it may be assumed that an activity event occurs when a neurotransmitter vesicle is released within a time interval in the first place. Further, it may be assumed that an activity event is present if at least one (or more generally: more than a pregiven minimal number) released neurotransmitter vesicle is present in an inner hair cell.

In other words, an activity event is an event occurring in a single inner hair cell. Typically, an activity event becomes noticeable in a local minimum or maximum on one of the uncleared temporal devolutions $A_1(t)$ to $A_n(t)$ or in exceeding, or falling below, a threshold value.

Further, a nerve activity pattern at a plurality of inner hair cells of an auditory model may also be used as a uncleared activity pattern. In this context, the nerve activity pattern describes the activity, or the temporal devolution of the activity, on plural different nerve fibers coupled to plural different inner hair cells. For example, each temporal devolution $A_i(t)$ is allocated to a temporal devolution of a potential, or a voltage, at a nerve fiber coupled to an i-th inner hair cell. Here, action potentials occur on the single nerve fibers, whose occurrence is described by the uncleared temporal devolutions $A_i(t)$. In this case, by an activity event the occurrence of an action potential on one of the n considered nerve fibers is meant.

Thus, in summary, it may be established that in a method according to the flow diagram 200, different quantities 252, 260, 268, 276 may be calculated for a plurality of different inner hair cells, wherein an activity pattern is formed by a summarization of the same quantity for a plurality of different hair cells.

Figure 3:
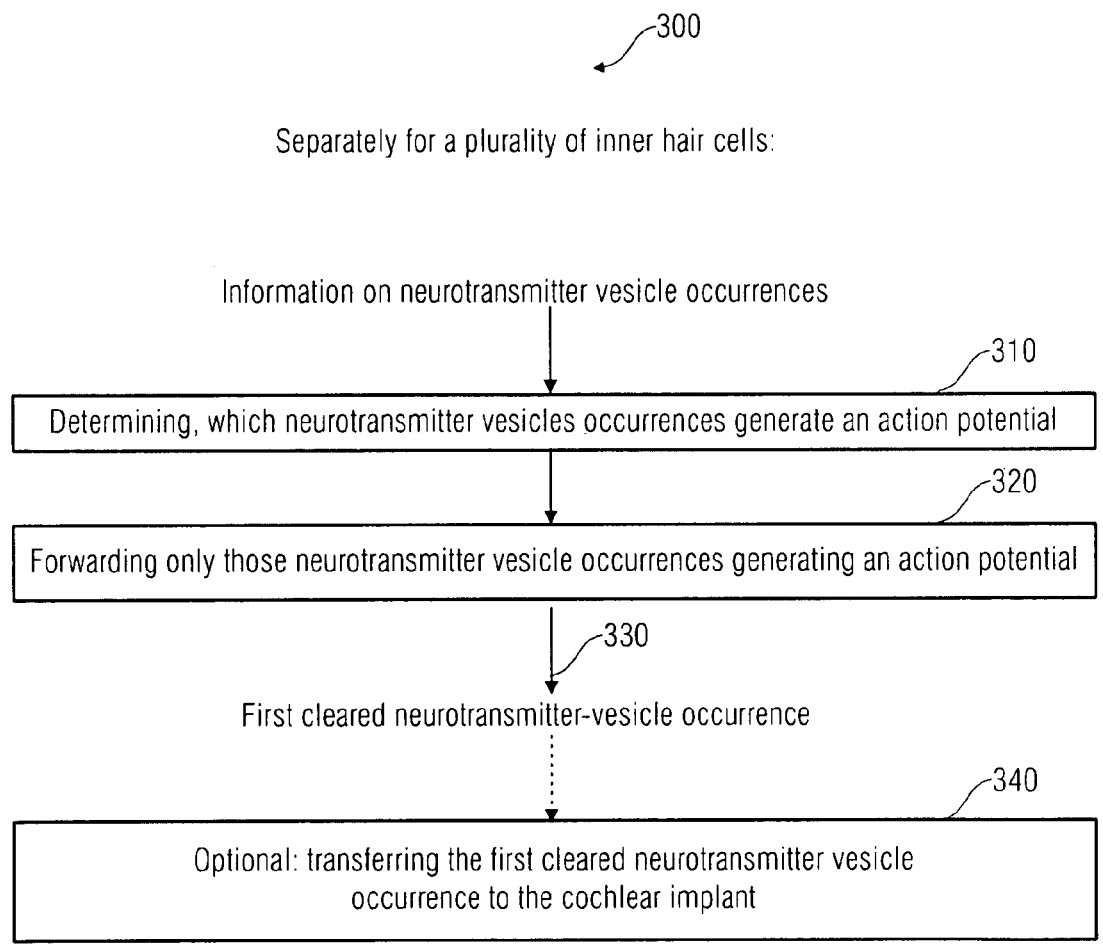
FIG. 3 is a flow diagram of an inventive method for determining a first cleared neurotransmitter vesicle occurrence from information on a neurotransmitter vesicle occurrence.

In the following, it will be described with reference to a concrete example how cleared temporal devolutions $A_{i,cl}(t)$ are generated from the uncleared temporal devolutions $A_i(t)$. Thus, FIG. 3 shows a flow diagram of an inventive method for determining a first cleared neurotransmitter vesicle occurrence from information on a neurotransmitter vesicle occurrence. In its entirety, the method in FIG. 3 is designated 300.

Typically, method 300 of FIG. 3 is performed separately in parallel for a plurality of inner hair cells. For simplicity, however, method 300 will here be only shown for a single inner hair cell. As an input quantity, method 300 receives information on a neurotransmitter vesicle occurrence in an inner hair cell of an auditory model. As described above, the neurotransmitter vesicle occurrence may describe a number of neurotransmitter vesicles present, on the average, in a time interval in the pre-synaptic or post-synaptic part of the inner hair cell, for example. Further, the neurotransmitter vesicle occurrence may describe how many neurotransmitter vesicles are released in a particular period of time or arrive at a particular location (e.g. in the synaptic cleft). The neurotransmitter vesicle occurrence is given by a temporal devolution, either in a time-continuous or a time-discrete form. In other words, the corresponding quantities mentioned above are provided either time-continuously or for a plurality of time intervals.

In the following, a presence of a neurotransmitter vesicle occurrence will describe that the corresponding quantity (number of present or released neurotransmitter vesicles) takes on a non-diminishing value, that is, different from zero.

In the first step 310, it is determined which neurotransmitter vesicle occurrences of the temporal devolution of the neurotransmitter vesicle occurrences generate an action potential. In other words, the temporal devolution of the neurotransmitter vesicle occurrence is analyzed, and it is those neurotransmitter vesicle occurrences which actually generate an action potential, or alternatively at least contribute to a generation of an action potential, that are determined (irrespectively of whether this is described by a time-continuous or a time-discrete devolution of values).

In this context, it should be understood that not every released neurotransmitter vesicle automatically results in an action potential. In some cases, for example, it is necessitated for the release of an action potential that at least two neurotransmitter vesicles (or at least a pregiven number of neurotransmitter vesicles) occur within a particular time interval.

In contrast, if only one neurotransmitter vesicle occurs in the corresponding time interval, this single neurotransmitter vesicle occurrence will still be rated as an activity event in the uncleared activity pattern. However, the single one neurotransmitter vesicle does not result in an action potential, since no further neurotransmitter vesicles occur in the considered inner hair cell within the pregiven time interval. Generally speaking, it may thus be established that a neurotransmitter vesicle occurrence does not generate any action potential, for example, if not at least a pregiven number of neurotransmitter vesicles occurs within a pregiven time interval subsequently to the corresponding neurotransmitter vesicle.

In other words, for example, the devolution of the neurotransmitter vesicle occurrences may be analyzed for different intervals (advantageously time-overlapped). For neurotransmitter vesicles which do not lie in at least one time interval in which more than a pregiven number of neurotransmitter vesicles is present on the whole, it is established that the corresponding neurotransmitter vesicles do not generate any action potential, and the corresponding neurotransmitter vesicle occurrences are not accepted to the first cleared information.

Further, it should be understood that subsequently to the release of an action potential due to a neurotransmitter vesicle occurrence, a so-called refractory period occurs, during which new neurotransmitter vesicle occurrences are ineffective. Thus, if it is established by an analysis of the neurotransmitter vesicle occurrence, which may also include a determination at which points in time action potentials are generated based on the neurotransmitter vesicle occurrence, that particular neurotransmitter vesicle occurrences lie within a refractory period (subsequently to the release of an action potential), then it will be established for the particular neurotransmitter vesicle occurrences that they do not generate any action potential.

Thus, if it is known which neurotransmitter vesicle occurrences do not generate any action potential or do not contribute to generating any action potential, then it may be concluded therefrom which neurotransmitter vesicle occurrences generate an action potential or at least contribute to the generation of an action potential.

Thus, a second step 320 includes forwarding only those neurotransmitter vesicle occurrences generating an action potential or contributing to a generation of an action potential. Thus, a first cleared neurotransmitter vesicle occurrence results, in which only neurotransmitter vesicles are contained which actually generate an action potential or at least contribute to the generation of an action potential.

The first cleared neurotransmitter vesicle occurrence is designated 330.

A fourth optional step 340 further includes transmitting the first cleared neurotransmitter vesicle occurrence to a cochlear implant.

Method 300 may be modified in various manners. For example, determining which neurotransmitter vesicle occurrences generate an action potential may be replaced with determining which neurotransmitter vesicle occurrences do not generate any action potential.

For example, determining which neurotransmitter vesicle occurrences generate an action potential or at least contribute to generating an action potential may include, for example, a complete deriving of action potentials from the temporal devolution of the neurotransmitter vesicle occurrence (that is, the information on the neurotransmitter vesicle occurrence). Based on the determination of the action potentials from the temporal devolution of the neurotransmitter vesicle occurrences, it may then be concluded which of the neurotransmitter vesicle occurrences contribute to a generation of an action potential. Furthermore, it may also be concluded which of the neurotransmitter vesicle occurrences directly lead to triggering an action potential. Each action potential may be uniquely traced back to a triggering neurotransmitter vesicle, and may be allocated to.

The associated triggering neurotransmitter vesicle occurrence may thus be considered a neurotransmitter vesicle occurrence generating an action potential. Thus, in the case just described, only those neurotransmitter vesicle occurrences which directly generate an action potential are forwarded in the second step 320. In other words, if plural neurotransmitter vesicles contribute to triggering an action potential, then only the last neurotransmitter vesicle occurrence, by which a potential threshold value for triggering a neurotransmitter vesicle is exceeded, will be forwarded.

On the other hand, it is also possible that all neurotransmitter vesicle occurrences contributing to generation of an action potential are forwarded when generating the first cleared neurotransmitter vesicle occurrence.

Triggering an action potential is coupled with the occurrence of a characteristic pattern in the activity pattern. Thus, an occurrence of a plurality of neurotransmitter vesicles within a particular period of time (i.e. a temporally "concentrated" occurrence of plural neurotransmitter vesicles) results in a release of an action potential. The corresponding characteristic pattern may thus also be directly recognized in the activity pattern.

In summary, it may thus be established that there are at least two possibilities for deciding which neurotransmitter vesicle occurrences are to be forwarded. For example, within the framework of the first backfiltration described with reference to FIG. 3, only those neurotransmitter vesicles generating an action potential may be stored and selectively forwarded to the cochlear implant. Alternatively, it is possible to accept all neurotransmitter vesicle occurrences which contribute to a generation of an action potential to the first cleared neurotransmitter vesicle occurrence, and to eliminate only those neurotransmitter vesicle occurrences from the uncleared neurotransmitter vesicle occurrence which do not contribute to a generation of an action potential, since they occur, for example, within a refractory period of the associated synapse, or the associated auditory nerve.

Figure 4:
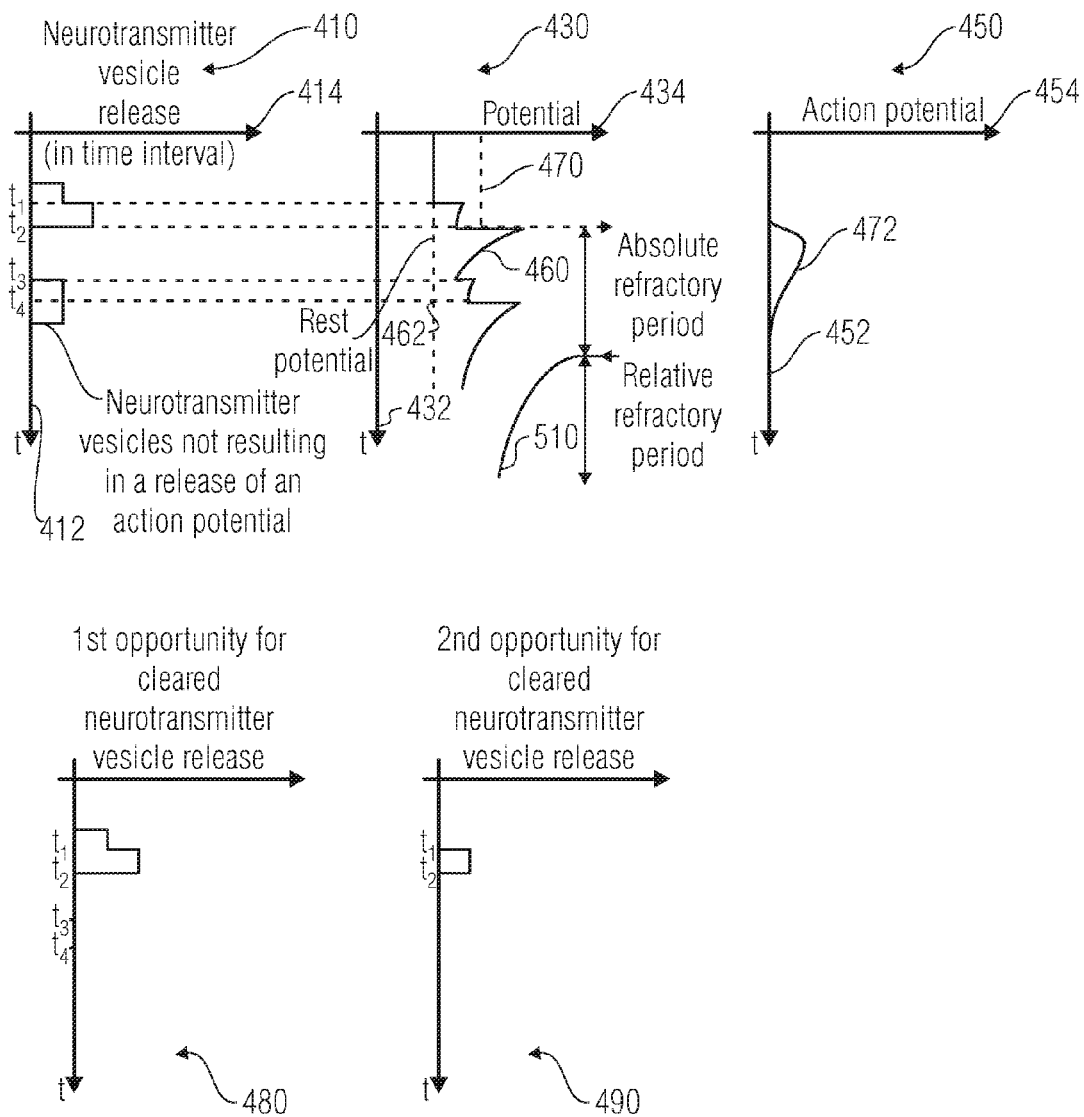
FIG. 4 is a schematic illustration of the flows when deriving a first cleared neurotransmitter vesicle occurrence from information on a neurotransmitter vesicle occurrence.

Further details related to this will be further described with reference to FIG. 4. FIG. 4 shows a schematic illustration of the flows when deriving a first cleared neurotransmitter vesicle occurrence from information on a neurotransmitter vesicle occurrence. A first graphic illustration 410 describes information on a neurotransmitter vesicle occurrence over time. Here, at an abscissa 412, time is plotted, while an ordinate 414 describes a neurotransmitter vesicle release per time interval. The neurotransmitter vesicle release per time interval advantageously takes on discrete values. A second graphic illustration 430 describes a potential in a synaptic cleft as a function of the time. Here, an abscissa 432 describes the time, while, in contrast, an ordinate 434 describes the potential. A third graphic illustration 450 shows a temporal devolution of an action potential on a nerve fiber, wherein the action potential is caused by the neurotransmitter vesicle release shown in the graphic illustration 410, or the post-synaptic potential shown in the graphic illustration 430. An abscissa 452, in turn, describes the time, while an ordinate 454 describes a voltage shape on a nerve fiber. A temporal devolution of the post-synaptic potential is designated 460.

In an equilibrium state, the post-synaptic potential takes on a rest potential 462. In response to a release of a neurotransmitter vesicle, the post-synaptic potential V increases to then to decrease again with a particular time constant. Thus, for example, a neurotransmitter vesicle release occurs at a point in time $t_1$, whereupon the post-synaptic potential V increases. For example, at a second point in time $t_2$, two further neurotransmitter vesicles are released, so that the post-synaptic potential V further increases and eventually exceeds a time-dependent threshold value 470. Thereupon, an action potential is triggered on the nerve fiber, as is apparent from the third graphic illustration (compare curve 472). While the time-dependent threshold potential 470 is almost constant before triggering an action potential, the time-dependent threshold potential 770 increases directly after triggering an action potential to a very high, or infinite, value and there remains during an absolute refractory period. Thus, during the absolute refractory period, no further triggering of an action potential is possible. Further neurotransmitter vesicle releases do occur at points in time $t_3$, $t_4$, leading to an increase in the post-synaptic potential V, however, no further action potential is released, since the synapse, or the nerve fiber, is within the absolute refractory period.

In this context, it should be further understood that the absolute refractory period is followed by a relative refractory period, during which the threshold potential 470 slowly returns back to the equilibrium value 462.

Based on the analysis described with reference to the graphic illustration 410, 430 and 450, there are two possibilities of deriving a cleared neurotransmitter vesicle release.

With the first approach, all those neurotransmitter vesicle releases contributing to a generation of action potentials are accepted to the cleared neurotransmitter vesicle release. For example, these are the neurotransmitter vesicle releases occurring subsequently to the points in time $t_1$ and $t_2$. In contrast, the neurotransmitter vesicle releases occurring at the points in time $t_3$ and $t_4$ are not accepted to the cleared neurotransmitter vesicle release. The neurotransmitter vesicle releases occurring at the points in time $t_3$ and $t_4$ do contribute to the increase in the post-synaptic potential V, too, however, the post-synaptic potential V decreases before the release of a next action potential to such extent that the neurotransmitter vesicle releases at the points in time $t_3$ and $t_4$ do not have any influence on the release of an action potential. In other words, the neurotransmitter vesicle releases at the points in time $t_3$ and $t_4$ influence the potential upon the occurrence of a next action potential to such a small extent that a point in time of an occurrence of a next action potential is influenced by the neurotransmitter vesicle occurrences at the points in time $t_3$ and $t_4$ at the most in an only negligible manner.

Thus, the graphic illustration 480 shows that only the neurotransmitter vesicle occurrences at the points in time $t_1$ and $t_2$, for example, are accepted to a cleared neurotransmitter vesicle occurrence.

A second graphic illustration 490 describes a second possibility for a cleared neurotransmitter vesicle release. Thus, it may be established that the release of the action potential 472 is made in response to the release of a neurotransmitter vesicle at the point in time $t_2$. In other words, the neurotransmitter vesicle occurring at the point in time $t_2$ "generates" the action potential 472, or directly triggers the action potential 472. Thus, it is possible to only accept the neurotransmitter vesicle actually triggering the action potential to a cleared neurotransmitter vesicle release. Thus, the graphic illustration 490 only shows a single neurotransmitter vesicle occurring at the point in time $t_2$ and yielding the deciding start for triggering an action potential 472.

In other words, a pattern is recognized in the neurotransmitter vesicle occurrence, which leads to triggering of an action potential, e.g. the presence of a number of shortly successive neurotransmitter vesicle occurrences. These are accepted to the cleared activity pattern. Further, it is recognized that a further neurotransmitter vesicle occurrence (at the points in time t3, t4) follows shortly after the first neurotransmitter vesicle occurrence (at the points in time t1, t2). The further neurotransmitter vesicle occurrence is not accepted to the cleared neurotransmitter vesicle occurrence. Thus, generally speaking, it is such characteristic patterns which lead to triggering of an action potential that are recognized in the activity pattern, for example, (directly by a pattern recognition or indirectly via deriving an intermediate quantity from the activity pattern, e.g. by a linear or non-linear filtration with a subsequent threshold value decision). Based on the recognition of a characteristic pattern, the cleared activity pattern is then ascertained.

Figure 5:
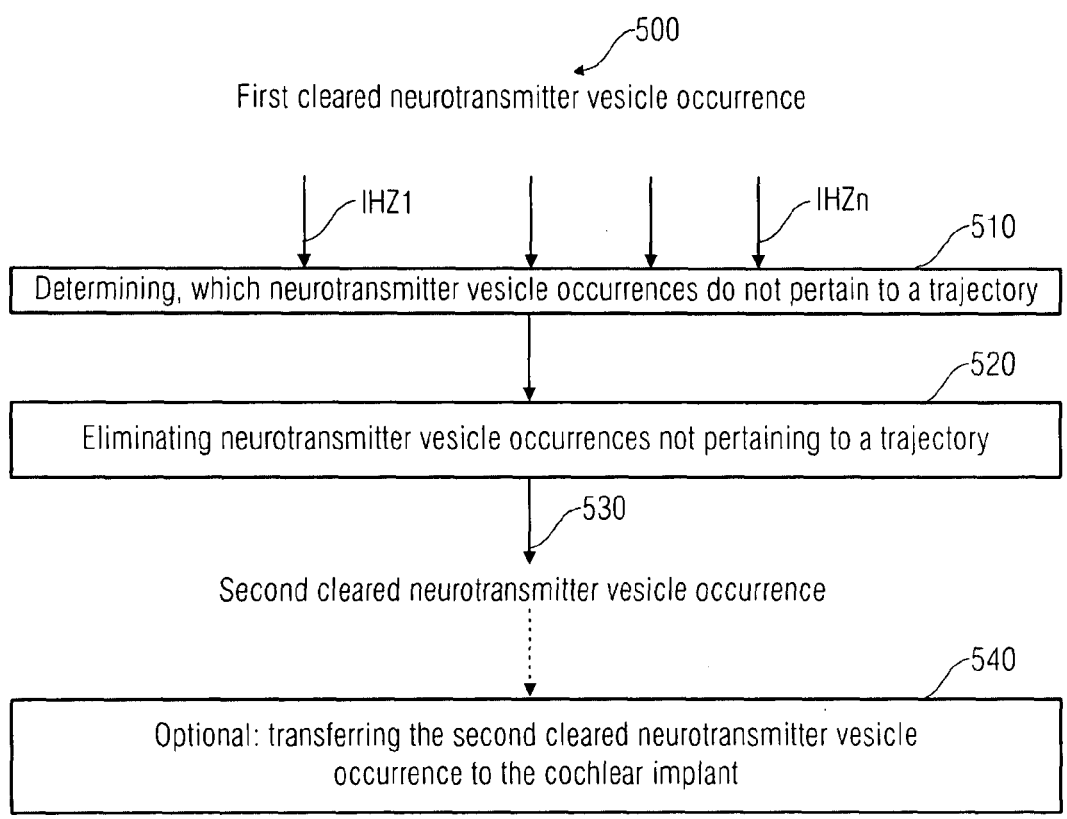
FIG. 5 is a flow diagram of an inventive method for deriving a second cleared neurotransmitter vesicle occurrence from a first cleared neurotransmitter vesicle occurrence.

In a further embodiment of the present invention, a further concept is employed, allowing to filter out information not relevant for intelligibility of speech from the activity pattern over time at the plurality of inner hair cells of an auditory model. For explaining this concept, FIG. 5 shows a flow diagram of an inventive method for deriving a second cleared neurotransmitter vesicle occurrence from the first cleared neurotransmitter vesicle occurrence. In its entirety, the inventive method of FIG. 4 is designated 500. Method 500 receives the first cleared neurotransmitter vesicle occurrence as input information, for example. Based on the first cleared neurotransmitter vesicle occurrence, in a first step 510, it is determined which neurotransmitter vesicle occurrences do not belong to a trajectory. In a second step 520, neurotransmitter vesicle occurrences which do not belong to a trajectory are eliminated to generate a second cleared neurotransmitter vesicle occurrence 530. Optionally, in a further step 540, the second cleared neurotransmitter vesicle occurrence may be transmitted to the cochlear implant.

Here, it should be understood that in the method 500, the first cleared neurotransmitter vesicle occurrence is processed simultaneously and in a coupled manner at plural inner hair cells (IHC1 to IHCn). When determining 510 which neurotransmitter vesicle occurrences do not belong to a trajectory (or which neurotransmitter vesicle occurrences belong to a trajectory), the neurotransmitter vesicle occurrences are jointly processed at plural inner hair cells, since a trajectory necessitates activity events to be present at a plurality of inner hair cells.

To facilitate understanding of the method 500, in the following, the structure of the cochlea as well as the development of trajectories, or delay trajectories, will be briefly explained.

Figure 6:
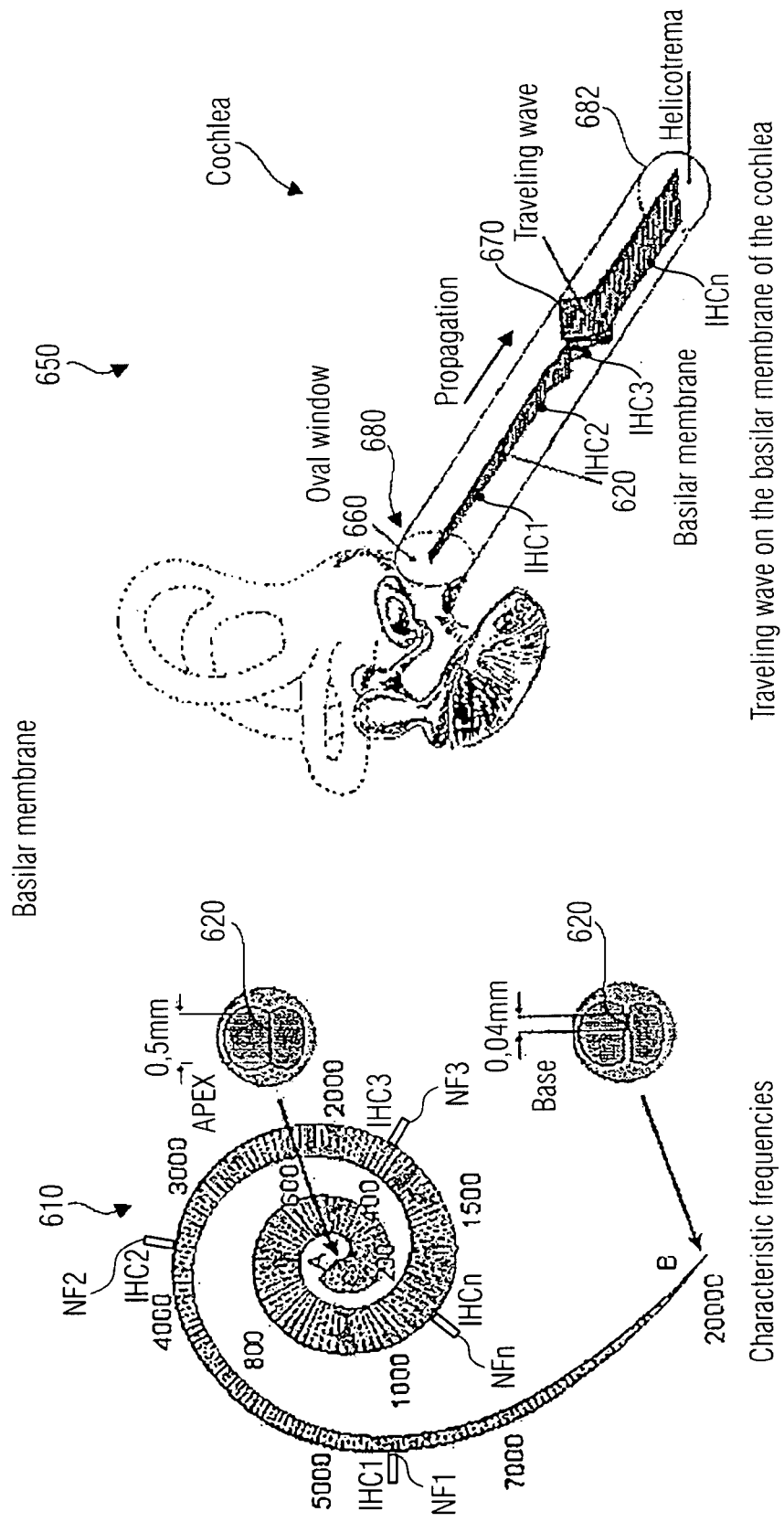
FIG. 6 is a graphic illustration of a geometry of the basilar membrane and a reaction of the basilar membrane to an excitation.

For this purpose, FIG. 6 shows a graphic illustration of a geometry of the basilar membrane and a reaction of the basilar membrane to an excitation.

A first graphic illustration 610 shows that a width of a basilar membrane 620 increases from the basis of the cochlea towards the end (apex) of the cochlea approximately by the factor 10. The graphic illustration 610 further shows different characteristic frequencies (in hertz), with regard to which there is a peak sensitivity at different locations of the cochlea. In the proximity of the basis of the cochlea, frequencies on the order of 20,000 hertz are perceived the strongest. Viewed from the basis of the cochlea, the frequency for which a maximum peak sensitivity results continuously decreases. The graphic illustration 610 further shows four exemplary inner hair cells IHC1, IHC2, IHC3, IHCn arranged along the cochlea and coupled with associated nerve fibers NF1, NF2, NF3, NFn. Assuming a sinus-shaped excitation of the cochlea, thus, the first inner hair cell IHC1 responds the strongest upon an excitation with a frequency of approximately 6,000 Hz, for example. In contrast, the second inner hair cell IHC2 comprises a peak sensitivity upon an excitation with a frequency of approximately 3,300 Hz. By analogy, the remaining inner hair cells IHC3, IHCn comprise other frequencies of a peak sensitivity.

A second graphic illustration 650 further describes coupling of an acoustic wave into the cochlea via an oval window 660. The coupling-in via the oval window 660 generates a traveling wave 670 in the cochlea, running from a basis 680 of the cochlea to an apex 682 of the cochlea and deflecting the basilar membrane 620 in this process. The nerve cells located nearer to the basis 680 the cochlea are excited earlier than nerve cells more remote from the basis 680 of the cochlea. In other words, the location of the traveling wave 670 as a function of time may be considered as a trajectory of the traveling wave 670. However, the trajectory may also be mapped to discrete nerve cells, so that a trajectory will also describe in which temporal sequence plural spatially separated nerve cells are excited by a traveling wave.

In the example shown, the inner hair cell IHC1, for example, is excited earlier by traveling wave 670 than the other inner hair cells IHC2, IHC3, IHCn. The first inner hair cell IHC1 is located more closely to the oval window 660, with the traveling wave 670 propagating from the oval window (i.e. from the basis 680 of the cochlea) to the apex 682 of the cochlea. Thus, the first inner hair cell IHC1, the second inner hair cell IHC2, the third inner hair cell IHC3 and the n-th inner hair cell IHCn are excited one after the other. In other words, a single traveling wave generates activity events at the shown inner hair cells in a temporal sequence, wherein the time intervals are determined by the propagation speed of the traveling wave 670 and the position of the corresponding inner hair cells IHC1, IHC2, IHC3, IHCn. However, it should be established that the activity events at the inner hair cells (when considered in a two-dimensional representation in dependence on the time and the index i of the inner hair cells IHCi form a trajectory corresponding to a time trajectory of a location of a maximum deflection of the traveling wave 670.

Figure 7:
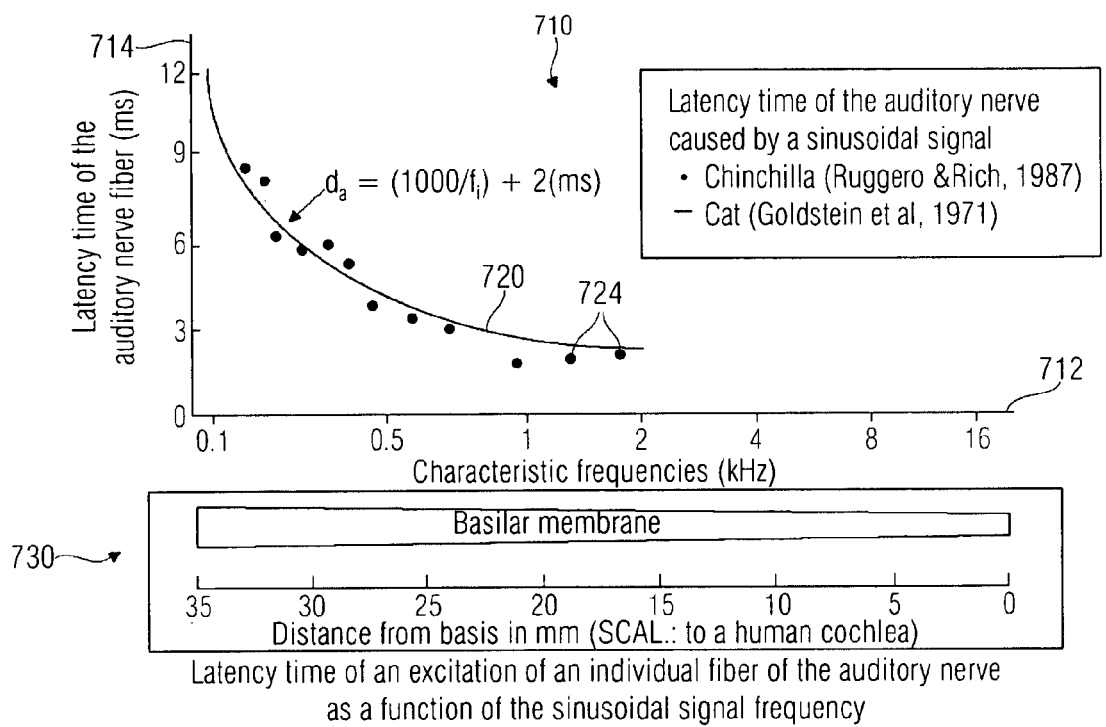
FIG. 7 is a graphic illustration of a delay in a propagation of audio signals of a different frequency from a basilar membrane.

For further explanation, FIG. 7 shows a graphic illustration of a delay in propagation of audio signals of a different frequency on a basilar membrane. A first graphic illustration 510 describes a latency time of auditory nerve fibers as a function of a characteristic frequency. Here, a frequency is plotted at an abscissa 712 in a range between 0.1 kHz and 16 kHz. An ordinate 714 describes a latency time of the auditory nerve fiber in a range between 0 and 12 ms. A curve 720 describes a devolution of a latency time of the auditory nerve caused by a sinus signal, over the frequency for a cat. Measurement points 724 describe a similar devolution for a chinchilla. It has been found that the latency time on auditory nerve fibers, as a function of a characteristic frequency $f_i$ for the concerned nerve fiber, may be described by the following equation:

$$b_a = (1000/f_i) + 2 \text{ ms}.$$

The corresponding connection is extensively explained e.g. in the article "A Space-Time Theory of Pitch and Timbre Based on Cortical Expansion of the Cochlea Traveling Wave Delay" by S. Greenberg, D. Poeppel and T. Roberts, presented at the XI$^{th}$ Int. Symp. on Hearing, Grantham. For details, thus, reference is made to the corresponding article.

It should be further understood that a second graphic illustration 730 shows a distance from hair cells belonging to a characteristic frequency to a basis of a human cochlea. Therefrom, in turn, it becomes apparent that hair cells belonging to high frequencies are located closely to the basis of the human cochlea, while hair cells belonging to low frequencies are located remotely to the basis of the human cochlea. The present illustration including the first graphic illustration 710 and the second graphic illustration 730, however, also shows that a latency time of the auditory nerve strongly increases for low frequencies (approximately under 0.5 kHz). Therefrom, it may be concluded that a propagation speed in the proximity of the end of the basilar membrane (i.e. remote from the basis of the cochlea) significantly decreases. The described latency time of the auditory nerve fibers results in a curvature of trajectories in activity patterns at inner hair cells, which are located at different locations of the cochlea.

Figure 8:
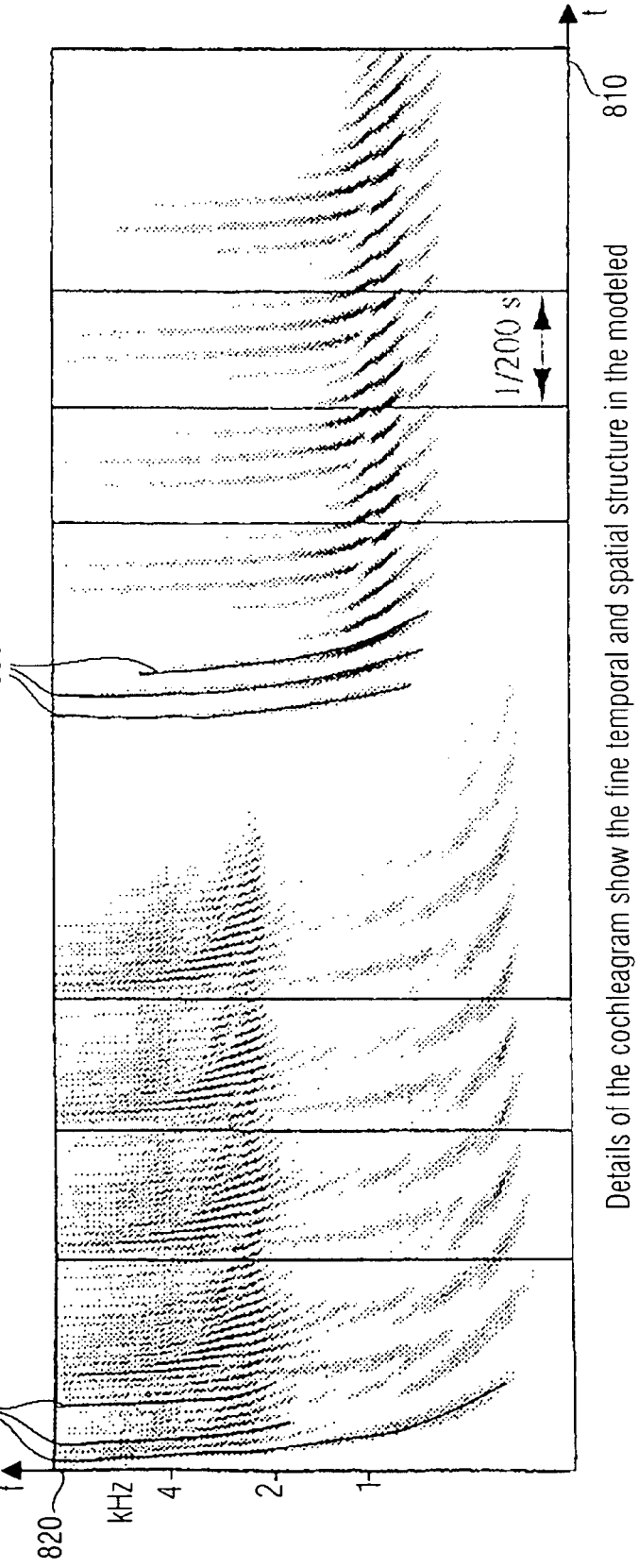
FIG. 8 is a graphic illustration of a cochleagram for a vocal "i"

For further explanation, FIG. 8 shows a graphic illustration of a cochleagram for a vocal "i" and for a non-harmonic tone complex of 700 Hz, 900 Hz and 1100 Hz, for example. Here, an abscissa 810 describes the time, while an ordinate 820 describes a frequency. The cochleagram itself describes the intensity of an excitation of different regions of the cochlea, which comprise a peak sensitivity for different frequencies. In other words, the cochleagram describes how strongly, and in which points in time, inner hair cells which comprise a peak sensitivity for different frequencies are excited. In other words, it may be concluded from the cochleagram when activity events occur in different hair cells. For example, if the cochleagram shows an activity at a frequency of 1 kHz, this means that for this point in time, activity events which comprise a peak frequency at a corresponding frequency of 1 kHz, for example, occur in an inner hair cell. The occurrence of the corresponding activity events in the hair cell with the peak sensitivity at 1 kHz is marked in the graphic illustration 800 with an "x", for example.

In the cochleagram 800 of the vocal "i", trajectories are clearly recognizable, of which some selected trajectories are marked and designated 850. In a similar manner, the cochleagram of the non-harmonic tone complex, too, shows trajectories designated 860.

Figure 9:
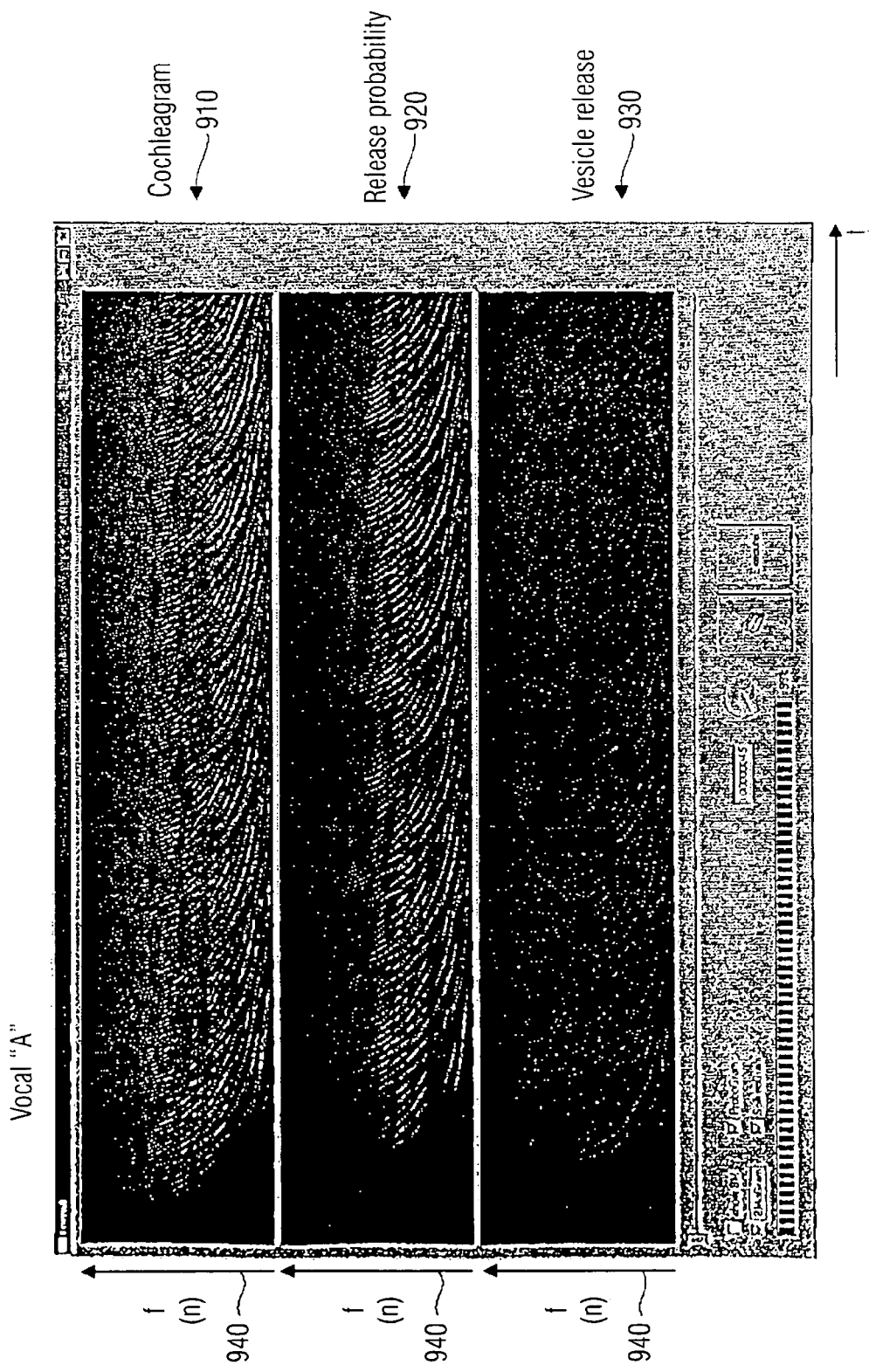
FIG. 9 is a graphic illustration of a cochleagram, a transmitter release probability and a transmitter vesicle release for a vocal "A"

FIG. 9 shows a further graphic illustration of a cochleagram as well as a transmitter release probability and a transmitter vesicle release for a vocal "A". Here, the cochleagram is shown in a first graphic illustration 910. A second graphic illustration 920 describes a transmitter release probability based on the cochleagram. The cochleagram describes an excitation of the basilar membrane over the time and the frequency or an excitation of different inner hair cells comprising a peak sensitivity for different frequencies, in dependence on the corresponding frequency of the peak sensitivity. As already described above, based on the cochleagram, a release probability for neurotransmitter vesicles may be calculated by an analysis of the mechanical, chemical and electrical processes in an inner hair cell. Further, based on the release probability k(t), a neurotransmitter vesicle release, or a neurotransmitter vesicle occurrence, may be calculated by a stochastic evaluation. An example of a corresponding neurotransmitter vesicle release, or a neurotransmitter vesicle occurrence, is shown in the third graphic illustration 930. Here, it is apparent that also the neurotransmitter vesicle release comprises characteristic trajectories over time and frequency. These trajectories are mapped to trajectories of action potentials (i.e. trajectories in the nerve activity pattern) by modeling the synaptic cleft. The frequency plotted at the ordinates 940 may be respectively assigned to associated hair cells, or nerve fibers (with an index i). Thus, the trajectories shown occur in a very similar form in the nerve activity pattern, too.

From the above explanations, it becomes apparent that clear trajectories occur at the activity patterns of the inner hair cells. In other words, in a representation of the activity pattern over time, line-shaped curves occur, which may be referred to as trajectories. Thus, a trajectory is a straight or curved line linking plural activity events in a two-dimensional representation of activity events over time and at a plurality of inner hair cells. Typically, a trajectory is a line linking plural activity events in the mentioned two-dimensional representation and not changing the direction of curvature in this context. Further, a trajectory is typically continuously differentiable at least once, that is, it has neither discontinuities nor bends. Advantageously, a trajectory is continuously differentiable even twice, that is, it has a constant or continuously changeable curvature.

Advantageously, a trajectory has at least approximately the shape of a hyperbola. Thus, a trajectory may be recognized by searching for a hyperbola-shaped curve. The other mentioned criterions, too, may be used for identifying a trajectory. By a hyperbola shape, the shape of a hyperbola in both a rectangular and an oblique two-dimensional coordinate system is meant.

Further, recognizing the presence of a trajectory may be made depending on the occurrence of a minimum number of activity events, for example, which at least approximately lie on a straight or curved line as defined above (if represented within the framework of a two-dimensional representation of an activity events of plural inner hair cells). Here, a tolerance limit may be pregiven and evaluated, defining how far (e.g. in the sense of a time interval) an activity event may be remote from an ideal trajectory, or line, to be still recognized as belonging to the trajectory.

With regard to the definition of (delay) trajectories, reference is made to the publication "A Space-Time Theory of Pitch and Timbre Based on Cortical Expansion of the Cochlea Traveling Wave Delay" by S. Greenberg and others (Proceedings of the XI$^{th}$ Int. Symp. on Hearing, Grantham, 1997). It has been shown that the motion of the basilar membrane proceeds in a well-defined manner from the basis (of the cochlea) to a location of a maximum deflection, behind which the motion is relatively fast attenuated. The passing of the traveling wave is extremely fast at the basis of the cochlea, yet dramatically slows down for peak deflections at the apex of the cochlea. Delay trajectories of the excitation of the cochlea, which are reflected in trajectories in the activity pattern, may be efficiently modeled by the following simple equation:

$$d_a = f_i^{-1} + k$$

Thus, the delay $d_a$ on the cochlea may be calculated using the given frequency $f_i$ and the delay constant k. The mentioned equation describes that the delay trajectories comprise a hyperbola-kind characteristic. In other words, a traveling wave on the basilar membrane, triggered by a particular acoustic event (e.g. a click), first causes activity events, comprising a peak sensitivity for high frequencies, in inner hair cells, and only later activity events, comprising a peak sensitivity for lower frequencies, in inner hair cells. Thus, a trajectory may generally be also construed as a line linking activity events at different inner hair cells, described in a two-dimensional time representation, which result due to a traveling wave on the basilar membrane or a wide-band click in the audio signal.

Figure 10A:
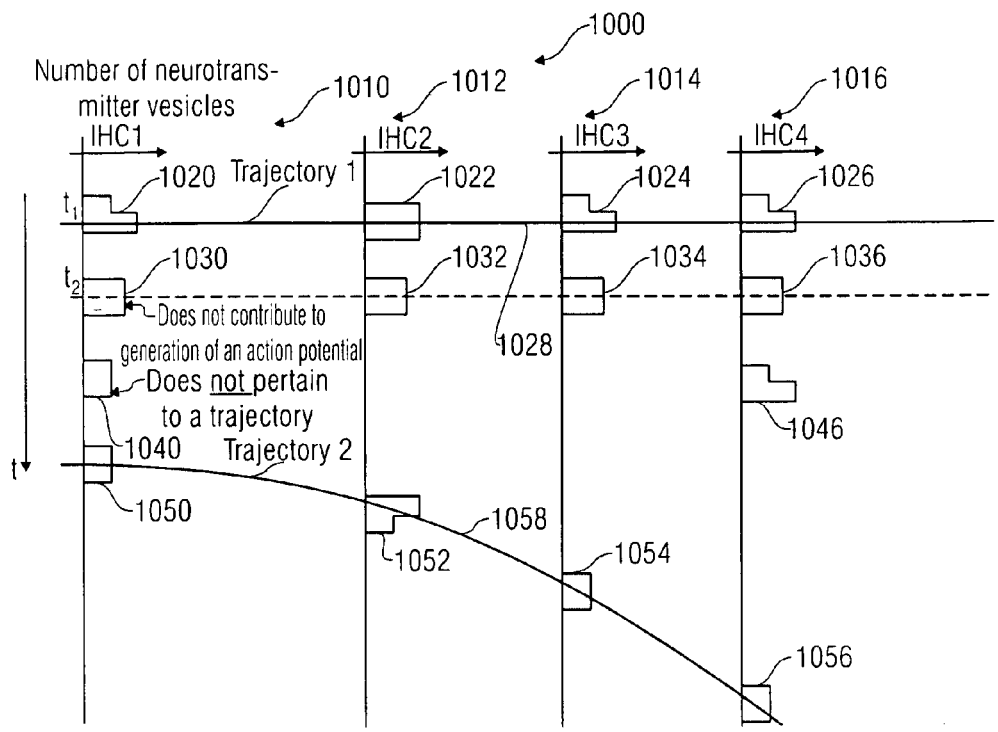
FIG. 10a is a graphic illustration of an activity pattern describing a neurotransmitter vesicle occurrence at a plurality of inner hair cells over time.

For further explanation of the inventive concept, FIG. 10a shows a graphic illustration of an activity pattern describing a neurotransmitter vesicle occurrence at a plurality of inner hair cells over time. In its entirety, the graphic illustration of FIG. 10a is designated 1000. In four temporal devolutions 1010, 1012, 1014, 1016, the graphic illustration shows the number of neurotransmitter vesicles occurring at respective synaptic clefts of a plurality of inner hair cells. In other words, the temporal devolution 1010 describes, for example, the number of neurotransmitter vesicles occurring at a first inner hair cell. By analogy, the second graphic illustration 1012 describes the number of neurotransmitter vesicles occurring at a second inner hair cell. The third graphic illustration 1014 shows the number of neurotransmitter vesicles occurring at a third inner hair cell, and the fourth temporal devolution 1016 shows the number of neurotransmitter vesicles occurring at a fourth inner hair cell. Here, it is assumed that the first inner hair cell IHC1 comprises a peak sensitivity for a first frequency, the second inner hair cell IHC2 comprises a peak sensitivity for a second frequency, the third inner hair cell IHC3 comprises a peak sensitivity for a third frequency, and the fourth inner hair cell IHC4 comprises a peak sensitivity for a fourth frequency, wherein the first frequency is larger than the second frequency, wherein the second frequency is larger than the third frequency, and wherein the third frequency is larger than the fourth frequency. The four inner hair cells IHC1 to IHC4 may be located, for example, either in a linear manner along the cochlea of an auditory system (e.g. human) or in a logarithmic manner. For example, the inner hair cells may be located such that the ratio of the first frequency and the second frequency is at least approximately equal to the ratio of the second frequency to the third frequency.

The number of neurotransmitter vesicles plotted in the temporal devolutions 1010, 1012, 1014, 1016 may describe, for example, the number of neurotransmitter vesicles released per unit of time. Equally, the temporal devolutions 1010, 1012, 1014, 1016 may also describe the number of the neurotransmitter vesicles on the whole present in a released form in the pre-synaptic or post-synaptic regions of the hair cell.

The temporal devolutions 1010, 1012, 1014, 1016 show that, e.g. at a time $t_1$, neurotransmitter vesicles 1020, 1022, 1024, 1026 occur at all four inner hair cells IHC1, IHC2, IHC3, IHC4. Thus, the four neurotransmitter vesicle occurrences may, in the representation over time and the plurality of inner hair cells, be connected by a straight line 1028. Thus, the straight line 1028 forms a first trajectory. At a second time $t_2$, relatively briefly after the first time $t_1$, again four neurotransmitter vesicles 1030, 1032, 1034, 1036 occur in the example. However, the neurotransmitter vesicles 1030, 1032, 1034, 1036 occur so briefly after the neurotransmitter vesicles 1020, 1022, 1024, 1026 that the synapses of the respective inner hair cells IHC1, IHC2, IHC3, IHC4 and/or the respective auditory nerve fibers are still in a refractory period at time $t_2$. That is, upon triggering an action potential due to a neurotransmitter vesicle occurrence, the synapse or the nerve fiber coupled to the synapse is not capable of outputting a further activity impulse, even if neurotransmitter vesicles are present. The graphic representation 1000 of FIG. 10 also shows a further neurotransmitter vesicle occurrence at the first inner hair cell IHC1, which is designated with 1040, as well as a further neurotransmitter vesicle occurrence 1046 at the fourth inner hair cell IHC4. The neurotransmitter vesicle occurrences 1040, 1046, however, do not pertain to a trajectory. For example, at the second inner hair cell IHC2 and the third inner hair cell IHC3, there are no neurotransmitter vesicles that lie, in the graphic illustration 1000, on a straight or curved connecting line of the neurotransmitter vesicle occurrences 1040, 1046, which forms a valid trajectory.

The representation 1000 also shows further neurotransmitter vesicle occurrences 1050, 1052, 1054, 1056 which, in the two-dimensional graphic representation 1000, may be connected by a temporally monotone connecting line 1058. In other words, the neurotransmitter vesicle occurrences 1050, 1052, 1054, 1056 lie on a trajectory 1058, as can easily be recognized in the graphic representation 1000. The fact that a trajectory is present may e.g. be recognized in that the times when the neurotransmitter vesicle occurrences 1050, 1052, 1054, 1056 take place correspond, in a monotone manner, to the locations of the four inner hair cells IHC1, IHC2, IHC3, IHC4 along the cochlea. In other words, the further one of the contemplated inner hair cells IHC1, IHC2, IHC3, IHC4 is located at the end of the cochlea, the later (in terms of time) the associated neurotransmitter vesicle occurrence 1050, 1052, 1054, 1056 takes place. The connecting line of the neurotransmitter vesicle occurrences 1050, 1052, 1054, 1056 further exhibits a uniform curvature, that is, does not change the direction of curvature. Furthermore, the presence of a trajectory may also be recognized in the fact that the connecting line 1058 exhibits, at least approximately, a hyperbolic shape.

Figure 10B:
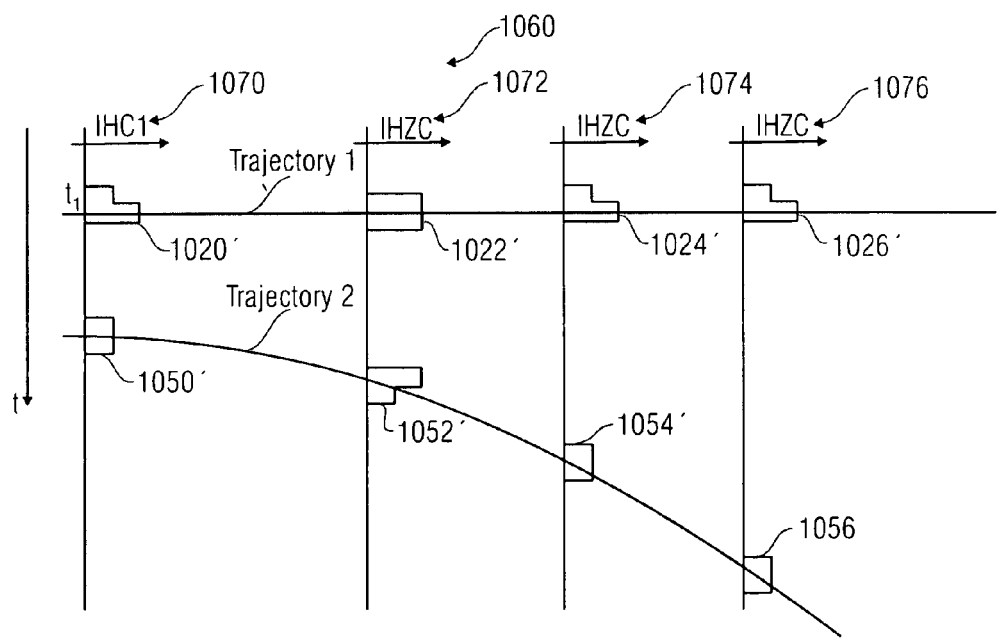
FIG. 10b is a graphic illustration of a cleared activity pattern describing a cleared neurotransmitter vesicle occurrence at a plurality of inner hair cells over time.

FIG. 10b further shows a graphic representation of a cleared activity pattern describing a cleared neurotransmitter vesicle occurrence at a plurality of inner hair cells over time. The graphic illustration of FIG. 10b is in its entirety designated with 1060. The graphic representation 1060 shows cleared temporal devolutions 1070, 1072, 1074, 1076 at the same four inner hair cells IHC1, IHC2, IHC3, IHC4, the graphic representation 1000 shows uncleared temporal devolutions for. The graphic representation 1060 shows that it is those neurotransmitter vesicle occurrences that are adopted into the cleared temporal devolutions 1070, 1072, 1074, 1076, which pertain to trajectories 1028, 1058. In the graphic representation 1060, the adopted neurotransmitter vesicle occurrences are designated with the same reference numerals as the original neurotransmitter vesicle occurrences in the graphic representation 1000, wherein the reference numerals of the adopted neurotransmitter vesicle occurrences have added thereto an "'", in the graphic representation 1060.

In other words, the cleared activity pattern shown in the graphic representation 1060 has adapted thereto those neurotransmitter vesicle occurrences that pertain to a trajectory. The other way round, it may also be asserted that those neurotransmitter vesicle occurrences not contributing to the generation of an action potential (neurotransmitter vesicle occurrences 1030, 1032, 1034, 1036) nor pertaining to a trajectory (neurotransmitter vesicle occurrences 1040, 1046) are removed from the cleared activity pattern of the graphic representation 1060. Furthermore, it is to be noted that e.g. the neurotransmitter vesicle occurrences 1030, 1032, 1034, 1036, which do not contribute to the excitation of an action potential, as a result do also not contribute to an intelligibility of speech. Furthermore, in some cases, neurotransmitter vesicle occurrences 1040, 1046 not pertaining to a trajectory do not, or to a slight extent only, contribute to an intelligibility of speech of e.g. vocals. This is because it has been found that the identification of vocals may be effected by an evaluation of the respective trajectories (e.g. 1028, 1058).

Figure 11:
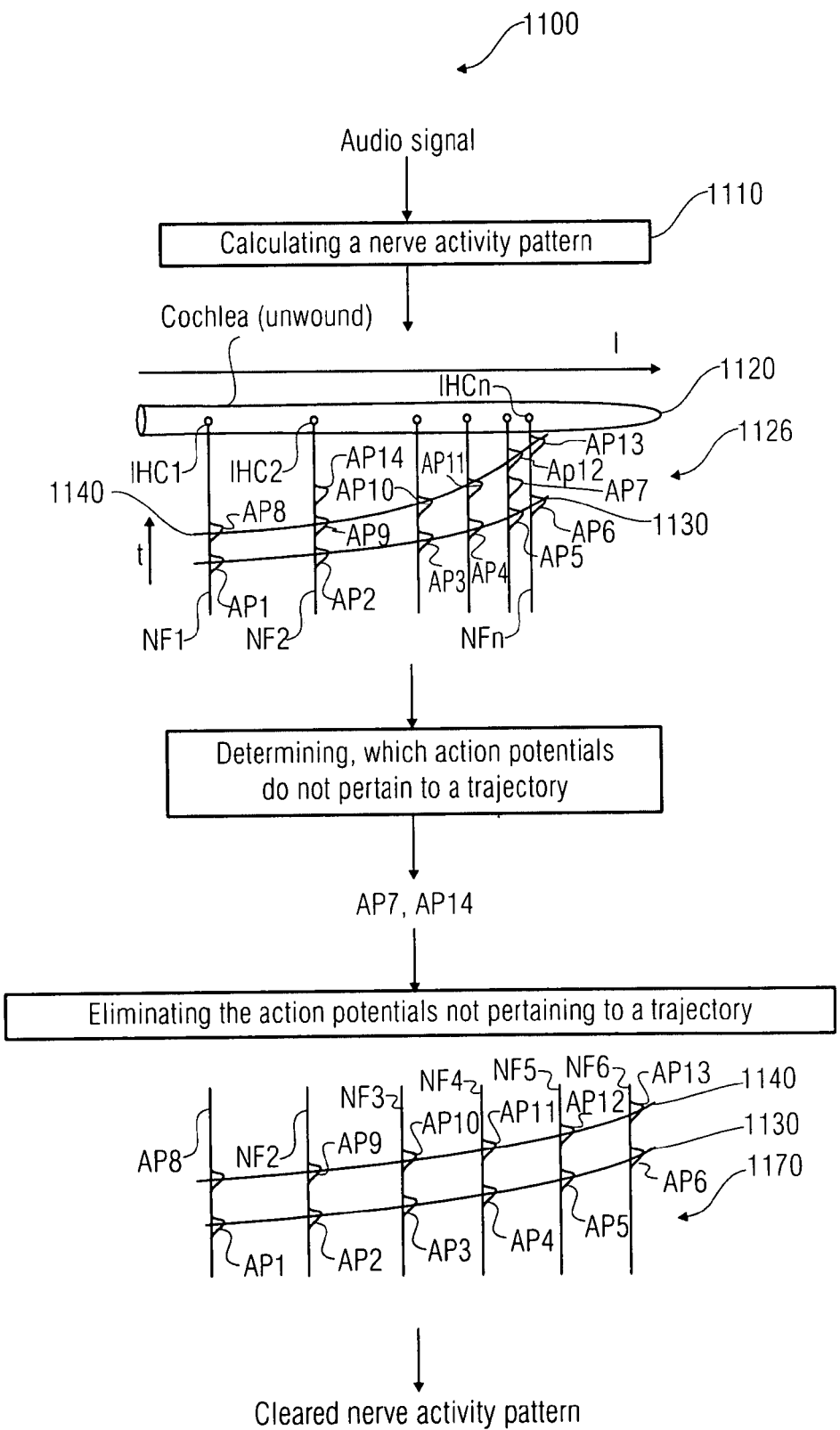
FIG. 11 is a flow diagram of an inventive method for deriving a cleared nerve activity pattern from an audio signal.

FIG. 11 shows a flow chart of an inventive method of deriving a cleared nerve activity pattern from an audio signal. The method of FIG. 11 is in its entirety designated with 1100. The inventive method includes a first step 1110, in which a nerve activity pattern is calculated based on the audio signal. The activity pattern describes an activity on a plurality of nerve fibers as a function of time. In other words, the nerve activity pattern describes several temporal devolutions of action potentials at a plurality of auditory nerve fibers of an auditory model. Alternatively, the nerve activity pattern may also describe a temporal devolution of a triggering of action potentials at a plurality of synaptic splits, which pertain to a plurality of inner hair cells. For clarity, the flow chart shows an unwound cochlea 1120 of a human auditory model together with a plurality of inner hair cells IHC1 to IHCn, arranged along the cochlea 1120 and exhibiting sensitivity peaks for different frequencies. The inner hair cells IHC1 to IHCn are coupled to associated nerve fibers NF1, NF2 to NFn and supply the associated nerve fibers NF1, NF2 to NFn with respective nerve activity impulses or action potentials. The action potentials are triggered by the release of neurotransmitter vesicles into a synaptic split via which the respective inner hair cell IHCi is coupled to an associated nerve fiber NFi. It can be seen that six action potentials AP1, AP2, AP3, AP4, AP5, AP6 generated by the cochlea 1020 lie on a first trajectory 1130. Further six action potentials AP8, AP9, AP10, AP11, AP12, AP13 lie on a second trajectory 1140. In the nerve activity pattern shown, which describes the action potentials on the plurality of inner hair cells IHC1 to IHCn over time, there, however, also occur two action potentials AP7, AP14 not pertaining to any trajectory. For the rest, reference is made to the above explanations for the definition of the trajectories. In other words, a trajectory in the nerve activity pattern is defined in the same way as a trajectory in a two-dimensional graphic representation of the neurotransmitter vesicle occurrence, wherein only the individual neurotransmitter vesicle occurrences are replaced by the respective action potentials.

The method shown in flow chart 1100 further includes a second step 1150 of determining, which of the action potentials described by the nerve activity pattern do not pertain to a trajectory 1130, 1140. In the example shown, the determining 1150 provides the action potentials AP7 and AP14 as a result.

The method 1100 further includes a third step 1160, in which action potentials not pertaining to any trajectory are eliminated in the nerve activity pattern. Here, either the original representation of the nerve activity pattern may be processed by cancelling or suppressing the action potentials not pertaining to any trajectory, or a copy of the original uncleared nerve activity pattern may be created, which only adopts action potentials pertaining to a trajectory 1130, 1140. Thus, what is produced is a cleared nerve activity pattern 1170, which, as an example, no longer includes nor describes the action potentials AP7, AP14 not pertaining to any trajectories but otherwise corresponds to the original uncleared nerve activity pattern 1126.

It therefore shows that the inventive method is applicable to different types of activity events occurring in a human or animal auditory system, for example to neurotransmitter vesicle occurrences or to action potentials. In this case, the activity pattern thus describes a temporal devolution of the respective quantity.

Figure 12:
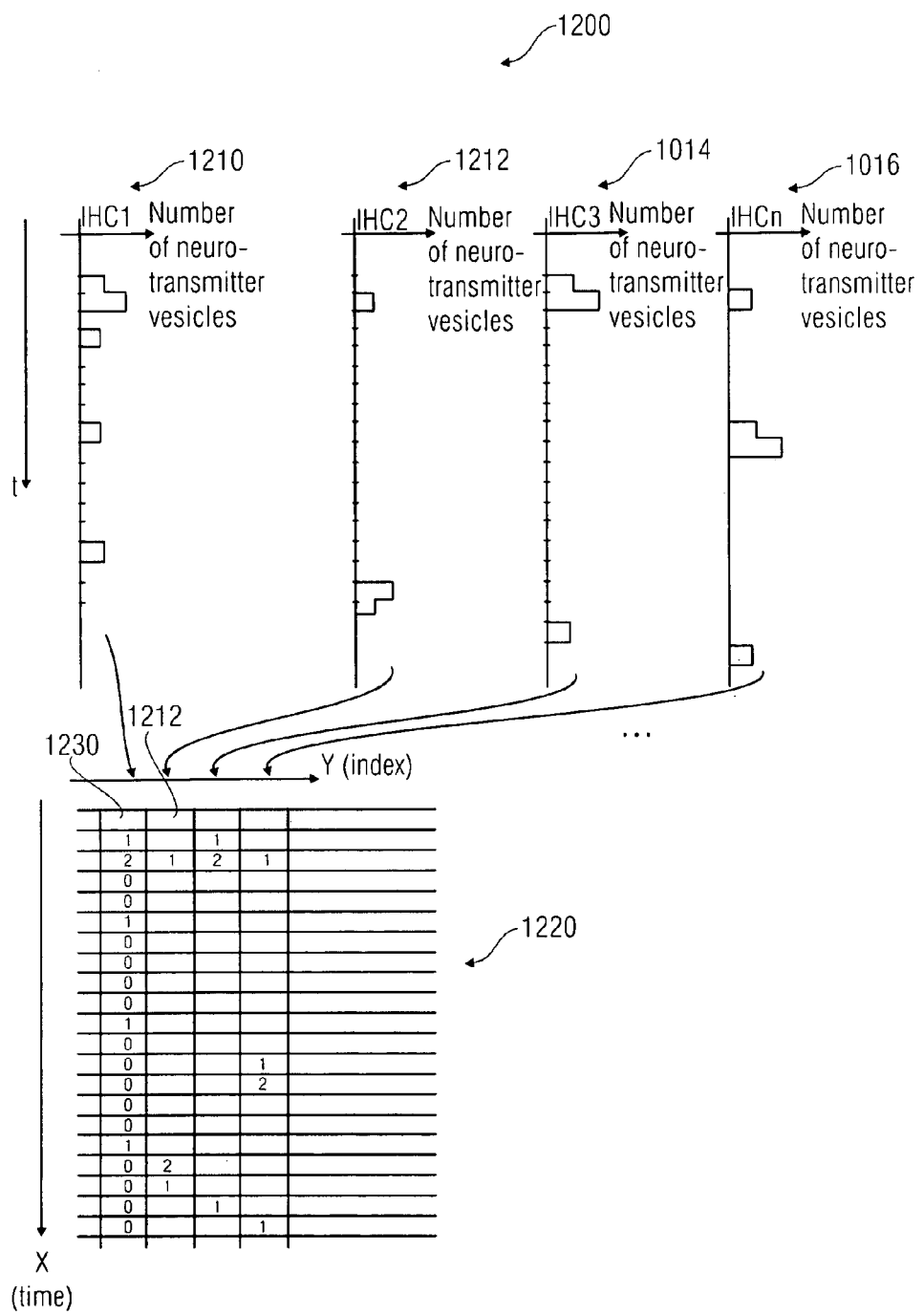
FIG. 12 is a schematic illustration of a procedure when generating a two-dimensional representation from an activity pattern over time at a plurality of inner hair cells of an auditory model.

FIG. 12 shows a schematic representation of a procedure for the creation a two-dimensional representation from an activity pattern over time at a plurality of inner hair cells of an auditory model. The schematic representation of FIG. 12 is in its entirety designated with 1200. In the exemplary procedure, temporal devolutions 1210, 1212, 1214, 1216 are received and converted to a two-dimensional, e.g. tabular, representation 1220. Here, the temporal devolutions 1210, 1212, 1214, 1216 describe e.g. the respective number of neurotransmitter vesicles at several inner hair cells, e.g. IHCn, in a manner analogous to FIGS. 10a and 10b. The temporal devolutions 1210, 1212, 1214, 1216 may be time-discretized, for example. Thus, the tabular representation 1220 describes the number of neurotransmitter vesicles released into the synaptic split in the time interval described by the respective row. Analogously, e.g. the second column 1232 of the table 1220 describes the second temporal devolution 1212.

Thus, the table 1220, for example, forms a two-dimensional representation of the activity events (e.g. of the number of neurotransmitter vesicles) over time of a plurality of inner hair cells.

Figure 13:
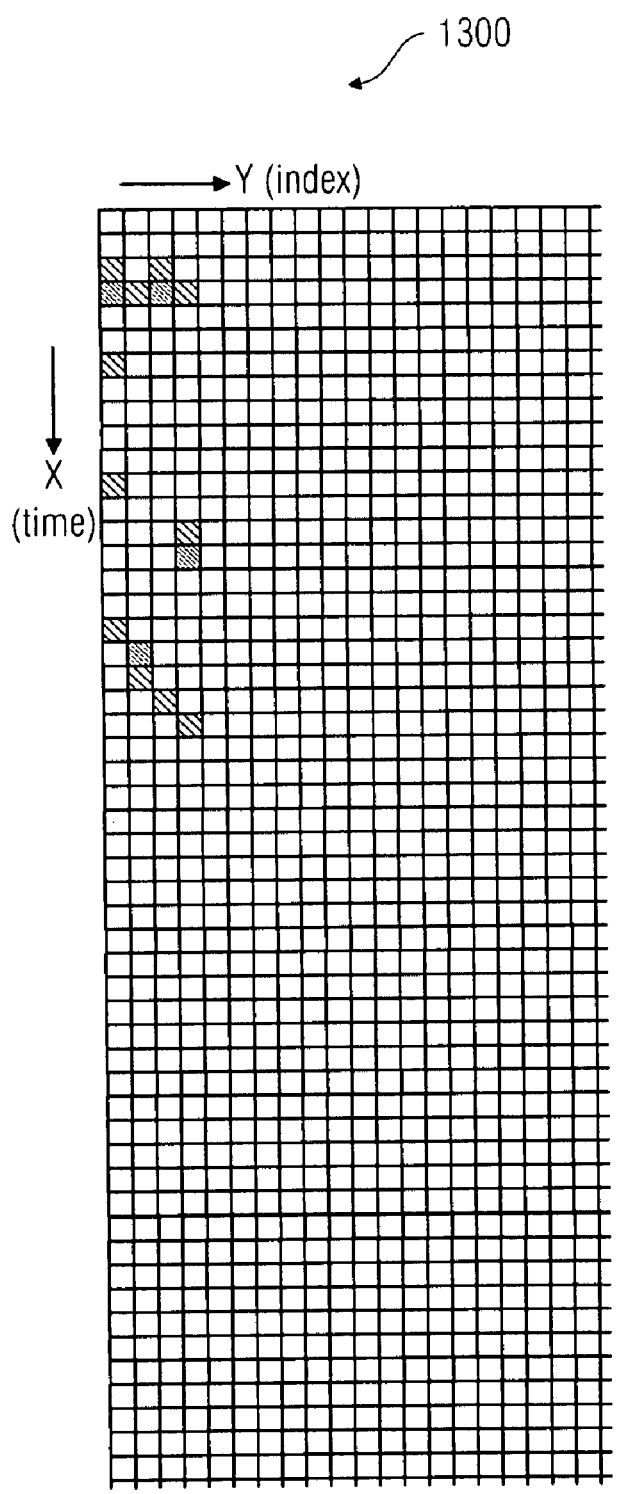
FIG. 13 is a second two-dimensional graphic illustration of an activity pattern over time at a plurality of inner hair cells of an auditory model.

For better illustration, FIG. 13 shows a further two-dimensional graphic representation of an activity pattern over time at a plurality of inner hair cells of an auditory model. The graphic representation of FIG. 13 is in its entirety designated with 1300. On the basis of the graphic representation 1300 of FIG. 13, it shows how the table 1220 according to FIG. 12, for example, may be converted to a representation of pixels and/or to what it extent the temporal devolutions 1210, 1212, 1214, 1216, which describe numbers of neurotransmitter vesicles at a plurality of hair cells, may be understood as a two-dimensional pattern.

Thus, the table 1120 may, for example, be understood as a description of a pattern of pixels, wherein a first dimension of the table (e.g. an x direction) corresponds to a first direction of the two-dimensional pattern 1300, and wherein a second dimension of the table corresponds to a second direction, e.g. a y direction. In other words, the first direction, that is the x direction in the two-dimensional representation, may correspond to e.g. the time, and the second direction, that is the y direction in the graphic representation 1300, may e.g. describe an index of the inner hair cells. Thus, the activity pattern over time, which describes the activity events at the plurality of inner hair cells over time, may be understood as a two-dimensional representation or a two-dimensional image pattern 1300, having new information added thereto in the first direction (x direction), with time advancing. Based on the interpretation of the activity pattern versus time as a two-dimensional diagram, which is described with respect to FIG. 13, it stands to reason that methods of pattern recognition may be applied to the activity pattern over time in order to recognize the trajectories described above.

Figure 14:
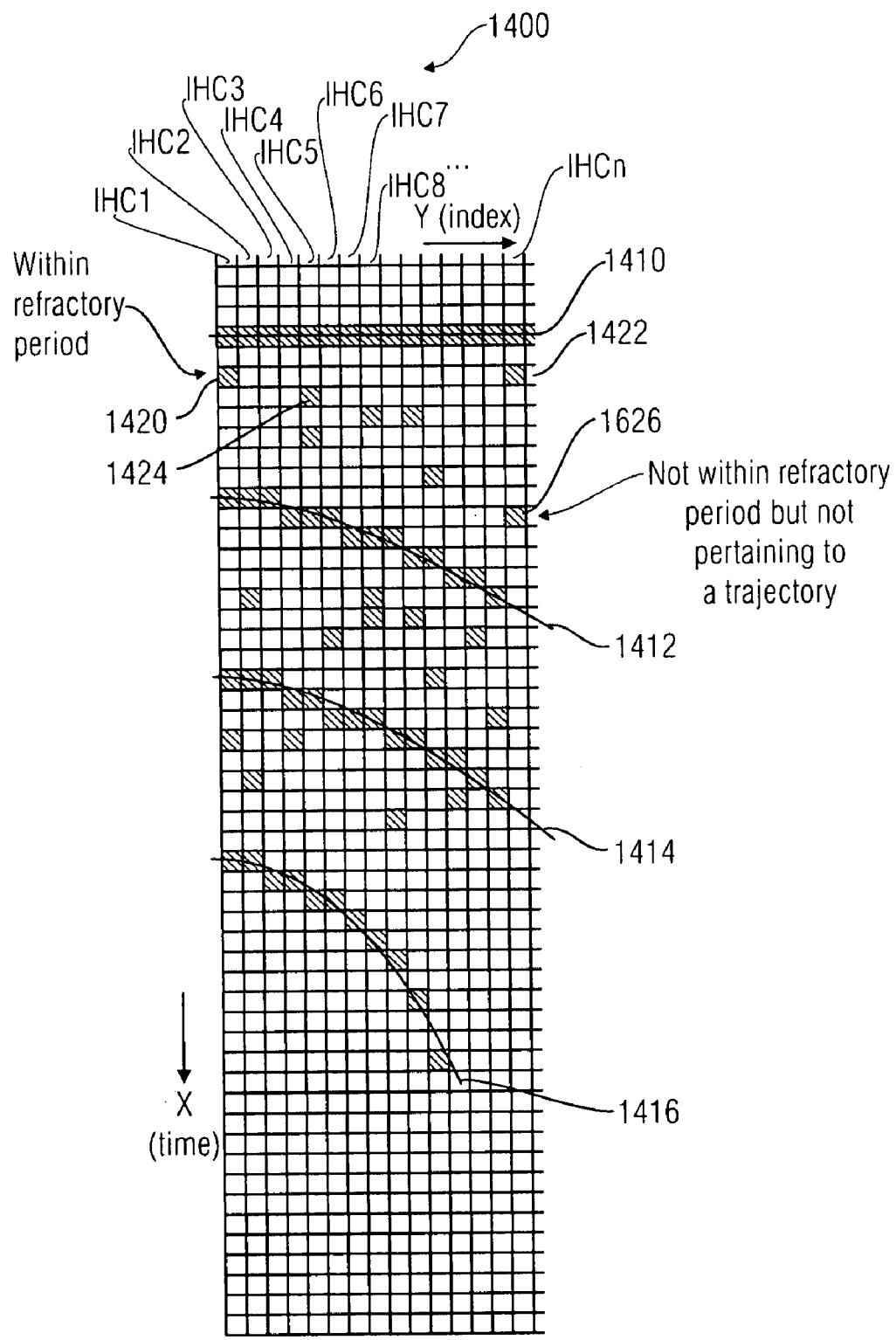
FIG. 14 is a third two-dimensional graphic illustration of an activity pattern over time at a plurality of inner hair cells of an auditory model.

For further illustration, FIG. 13 shows a third graphic representation of an activity pattern over time at a plurality of inner hair cells of an auditory model, wherein the activity pattern over time is again represented as a two-dimensional pattern of pixels. The two-dimensional pattern of FIG. 14 is in its entirety designated with 1400. Image columns of the two-dimensional image pattern 1400 are allocated to the activity events at different inner hair cells IHC1 to IHCn. The rows of the image pattern 1400 are further allocated to points in time and/or time intervals. Therefore, in the two-dimensional graphic representation 1400 of FIG. 14, straight as well as curved line segments 1410, 1412, 1414, 1416 are to be seen, each describing a trajectory in the activity pattern. The graphic representation 1400 also shows further individual activity events (e.g. activity events 1420, 1422, 1424, 1426) not pertaining to the trajectory or occurring within a refractory period of the associated synapse or the associated nerve fiber. For example, the activity event 1420 follows briefly after the occurrence of an activity event on the first inner hair cell IHC1 in the context of the first trajectory 1410. Therefore, the synapse of the nerve fiber NF1 coupled to the first inner hair cell IHC1 is in a dead time when the activity event 1420 occurs. It can therefore be recognized, in the context of a pattern recognition, that the activity event 1420, for example, is not relevant for an intelligibility of speech as it would, in a human auditory system, not result in a triggering of an action potential on a nerve fiber in the first place. Same applies to the activity event 1422.

Furthermore, there may be identified activity events not pertaining to any trajectory, that is not pertaining to any line-shaped curve in the graphic representation 400. This applies to the activity event 1426, for example. Therefore, in the context of the pattern recognition, which is applied to the pattern of the graphic representation 1410, it may be discovered that the activity event 1426 not pertaining to the trajectory is not relevant for the intelligibility of speech of at least one sound, for example.

Figure 15:
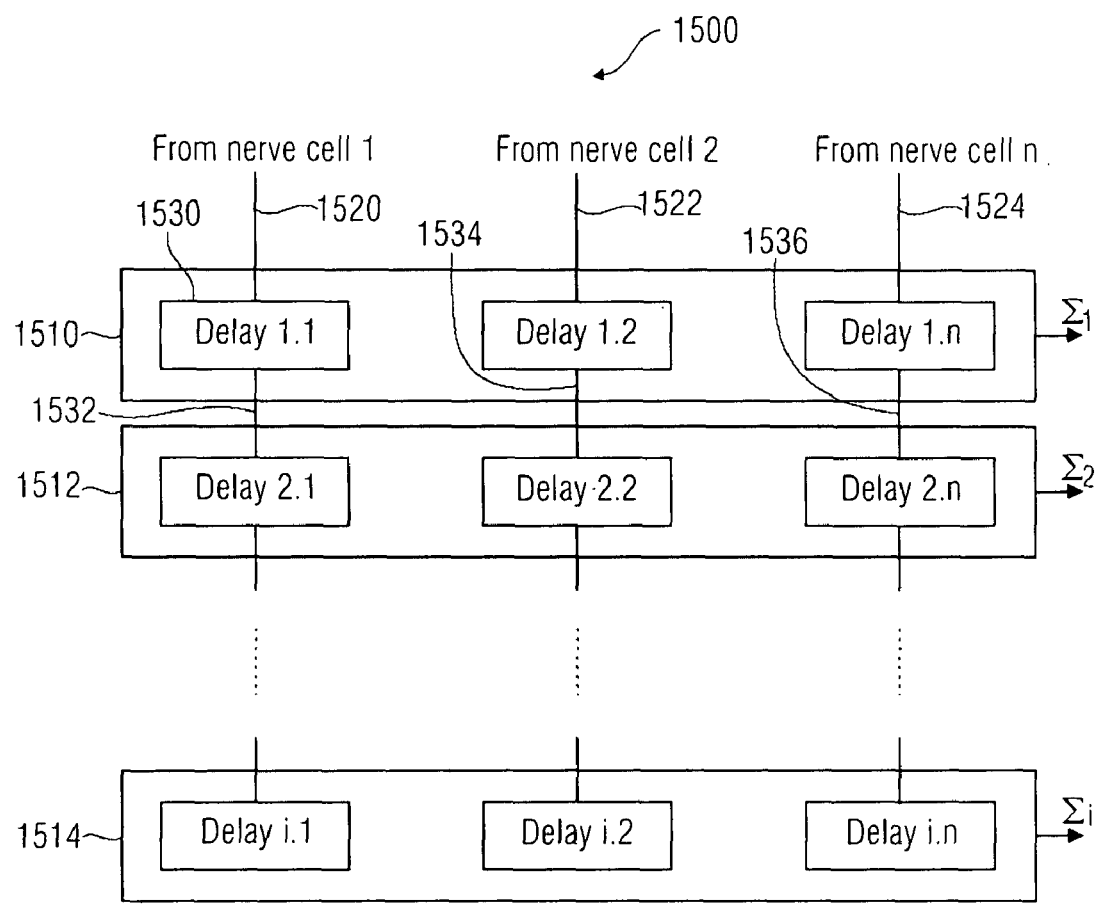
FIG. 15 is a block circuit diagram of a device for performing, according to the invention, a pattern recognition based on the activity pattern.

FIG. 15 shows a block diagram of a device for the inventive processing of the nerve activity pattern. The device shown in FIG. 15 is in its entirety designated with 1500. The device 1300 shown comprises a plurality of stages 1510, 1512, 1514, wherein the first stage 1510 receives parallel signals 1520, 1522, 1524 from nerve cells. The signals 1520, 1522, 1524 advantageously describe action potentials on nerve fibers coupled to the respective nerve cells or inner hair cells, and therefore describe the nerve activity pattern. However, the signals may also describe another activity pattern such as a neurotransmitter vesicle occurrence in a plurality of inner hair cells.

In a first stage 1510, the first nerve signal 1520, for example, is subjected to a delay in a first delay means 1530 and then forwarded to a second stage 1512 in the form of a delayed nerve signal 1532. In a similar manner, the second nerve signal 1522 is also delayed in the first stage 1510 and then forwarded to the second state 1512 in the form of a delayed nerve signal. The remaining nerve signals are also processed in the first stage 1510 in the same manner (including the n-th nerve signal 1524, for example).

The second stage 1512 is configured parallel to the first stage 1510 and therefore also enables a delayed forwarding of the delayed nerve signals 1532, 1534, 1536, thus creating nerve signals delayed twice. A device for the inventive processing of the nerve activity pattern comprises a plurality of stages connected in series and configured in the same manner as the first stage 1510 and the second stage 1512. The nerve signals 1520, 1522, 1524 are therefore forwarded through the plurality of stages 1510, 1512, 1514 in a parallel manner, wherein each stage adds an adjustable delay to the nerve signals.

Beyond that, each of the stages 1510, 1512, 1514 is configured to form a sum of the nerve signals going in and out of same (and/or of the nerve signals delayed m times). Furthermore, the stages 1510, 1512, 1514 are advantageously configured to compare this sum to an adjustable threshold value so as to ascertain whether, at a given time, at least one given number of nerve signals and/or delayed nerve signals (that is incoming nerve signals or outgoing nerve signals) are active (or exhibit an action potential).

It is further advantageous that the delays of the delay means present in the stages 1510, 1512, 1514 be differently adjusted so that a first nerve signal 1520, for example, in passing the stages 1510, 1512, 1514, is subject to another delay than the second nerve signal 1522. For example, delays may be adjusted such that different total delays are yielded for the nerve signals 1520, 1522, 1524, on passing the stages 1510, 1512, 1514 (wherein it is naturally admissible that two nerve signals are delayed in the same manner, for example). In other words, the means 1500 is advantageously configured such that the same delays are not yielded for all of the nerve signals. Apart from that, it is advantageous that, within the presence of j stages 1510, 1512, 1514, at least (j-1) stages 1510, 1512 are configured such that the delay means included in a stage do not all exhibit the same delay for the plurality of nerve signals. This serves to achieve that a nerve activity pattern entering an inventive means 1500 is distorted such over time in passing the means described that individual nerve signals are time-shifted relative to other nerve signals. By means of the distortion, linear patterns that are curved in a time representation, that is trajectories, may be straightened out in the nerve activity pattern.

Furthermore, it is to be noted that by the summation within a stage, the fact that an originally curved trajectory was bent such in the nerve activity pattern that a straight line was yielded may be recognized (wherein a straightened-out line is described and/or recognized by the fact that a given number of the delayed nerve signals exhibit an action potential almost simultaneously and/or in a temporally overlapping manner).

Figure 16:
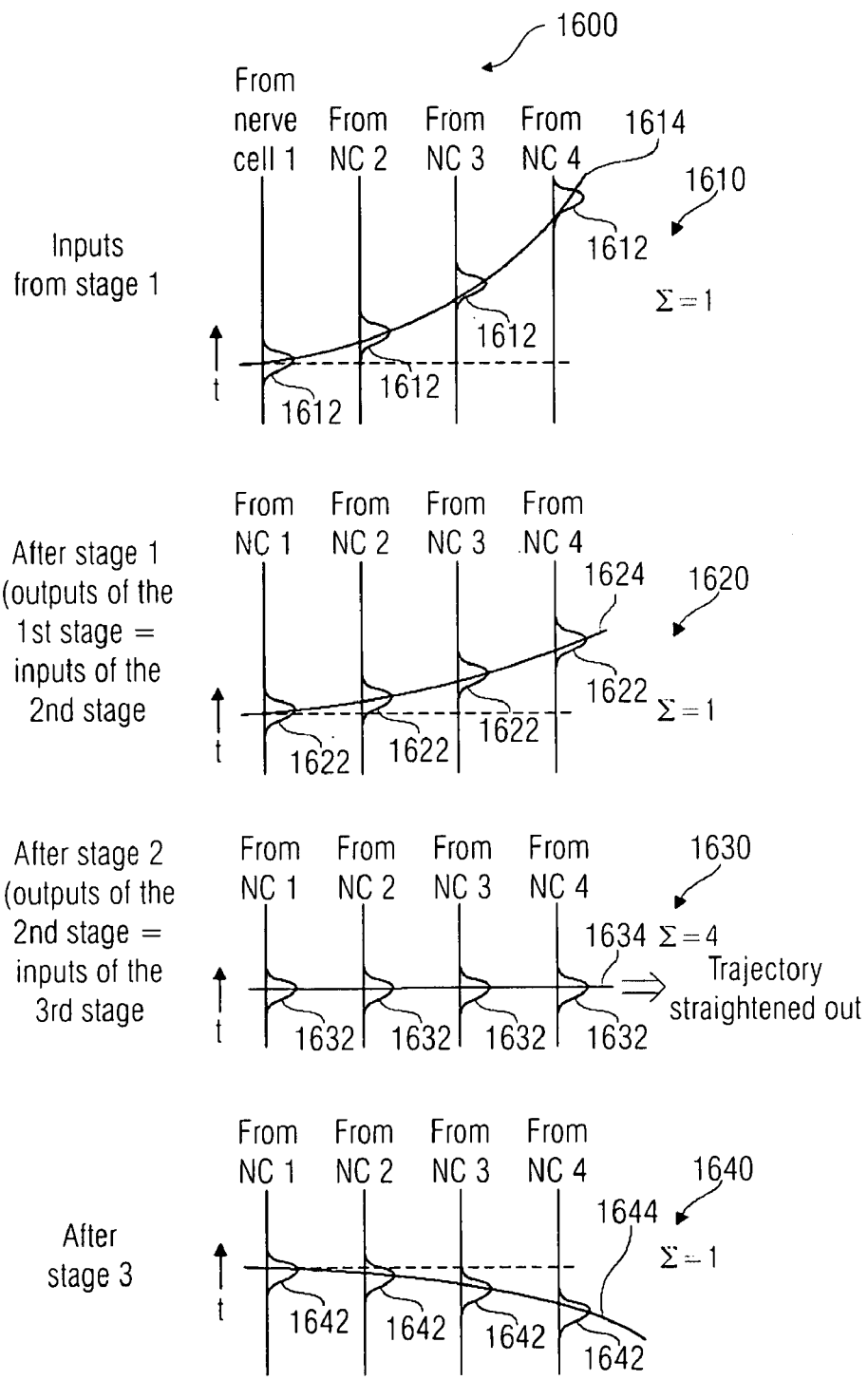
FIG. 16 is a graphic illustration of signals in a device for performing, according to the invention, a pattern recognition.

The mode of operation of the means 1500 is to be illustrated on the basis of FIG. 16. FIG. 16 shows an exemplary graphic representation of the signals in a device 1500 for the inventive processing of the nerve activity pattern. The graphic representation of FIG. 16 is in its entirety designated with 1600.

Here, a first graphic representation 1610 describes an exemplary nerve activity pattern at inputs of the device 1500. What is exemplarily shown is the signals from four nerve cells (or on four nerve fibers) in a temporal devolution. Apart from that, it is to be noted that the action potentials 1612 form a trajectory 1614. As shown, the trajectory 1614 exhibits a strong curvature in the time representation as the action potentials 1612 from the different nerve fibers exhibit a clear temporal offset at the inputs of the first stage 1510. Therefore, only one action potential is present in the first stage 1510 at each fixed time so that a threshold value for a sum of the action potentials present at the first stage, which is set to two, for example, is not exceeded. As a result, the first stage does not provide an output signal at a threshold-value output.

A second graphic representation 1620 describes the conditions at an output of the first stage 1510. It is assumed here that the nerve signal supplied by the first nerve cell NZ1 is delayed stronger in the first stage 1510 than the nerve signals supplied by the other stages. Beyond that, it is assumed that, in the example given, the nerve signal supplied by the fourth nerve cell NZ4 is delayed least, while the nerve signal from the third nerve cell NZ3 is delayed slightly more, and wherein the delay for the nerve signals from the nerve cells NZ2 and NZ1 is continuously increasing. Generally put, the signals pertaining to nerve cells that respond to a lower frequency are delayed less than nerve signals from nerve cells detecting higher frequencies.

The second graphic representation therefore again shows action potentials 1624 as a function of time, wherein the action potentials 1622 form a trajectory 1624. As can be seen in the second graphic representation 1620, the curvature of the trajectory 1624 at the outputs of the first stages is less than a (time/space and/or time/frequency) curvature of the trajectory 1616 at the inputs of the first stage. This is the result of the different delays of the nerve signals pertaining to different nerve cells in the delay means (e.g. 1530) of the first stage. Therefore, a curved trajectory is so to speak straightened out. As the second graphic representation 1620 shows, the second trajectory 1624 still exhibits a residual curvature so that the action potentials 1622 originating from different nerve cells or nerve fibers are not all simultaneously present at the outputs of the first stage 1510 and/or inputs of the second stage 1512.

The second stage 1512, too, effects a further delay, wherein signals from nerve cells which are sensitive to low frequencies are again delayed less than signals from nerve cells sensitive to higher frequencies. A third graphic representation 1630 shows the nerve signals that are delayed once again in the second stage 1512 at outputs of the second stage. The third graphic representation 1630 shows that, in the present example, the nerve signals at the outputs of a second stage are each delayed such that action potentials 1632 from several nerve cells are simultaneously present at the outputs of the second stage. In other words, a trajectory 1634 described by the action potentials 1632 is at least approximately straightened out. The action potentials 1632 therefore occur simultaneously or approximately simultaneously (at least, in any case, temporally overlapping) so that the simultaneous occurrence, by a summation of the signals present at the outputs of the second stage (or inputs of the third stage), exhibits a prominent peak large enough to exceed a given threshold value (e.g. two or three).

In other words, by appropriate summation means (or any other appropriate means) it may be recognized when a curved trajectory was straightened out. The respective information enables a conclusion both to the initial time of the trajectory and to the shape of the trajectory. That is, it can be ascertained after how many stages passed a trajectory was straightened. By means of this, and knowing the delays for the individual nerve signals in the stages of the means 1500, a conclusion may be made to an original shape of the trajectory also. Furthermore, the transit time for the stages is advantageously known so that the time when a trajectory entered the means 1500 may also be determined. Therefore, both characteristic time information of the trajectories and information on the shape and/or curvature of the trajectories may be ascertained in order to determine, which activity events pertain to a trajectory and/or which activity events do not pertain to a trajectory.

In addition, it is to be noted that a fourth graphic representation 1640, for enhancing understanding, also shows output signals at outputs of a third stage. Action potentials 1642 describe a trajectory 1644, which, however, is again curved by a further bending of the trajectory.

It is to be noted that the delays in the stages 1510, 1512, 1516 may be achieved in different ways. The delay means (e.g. 1530) may e.g. be clocked and/or they may be continuously or discretely adjustable delay means. In addition, it is also possible that one or more delay means in a given stage are deactivated for one or more nerve signals so that some nerve signals are forwarded through a stage with as little delay as possible. Apart from that, it is to be noted that the means 1500 in total may be implemented in the form of an analog or digital circuit.

Figure 17:
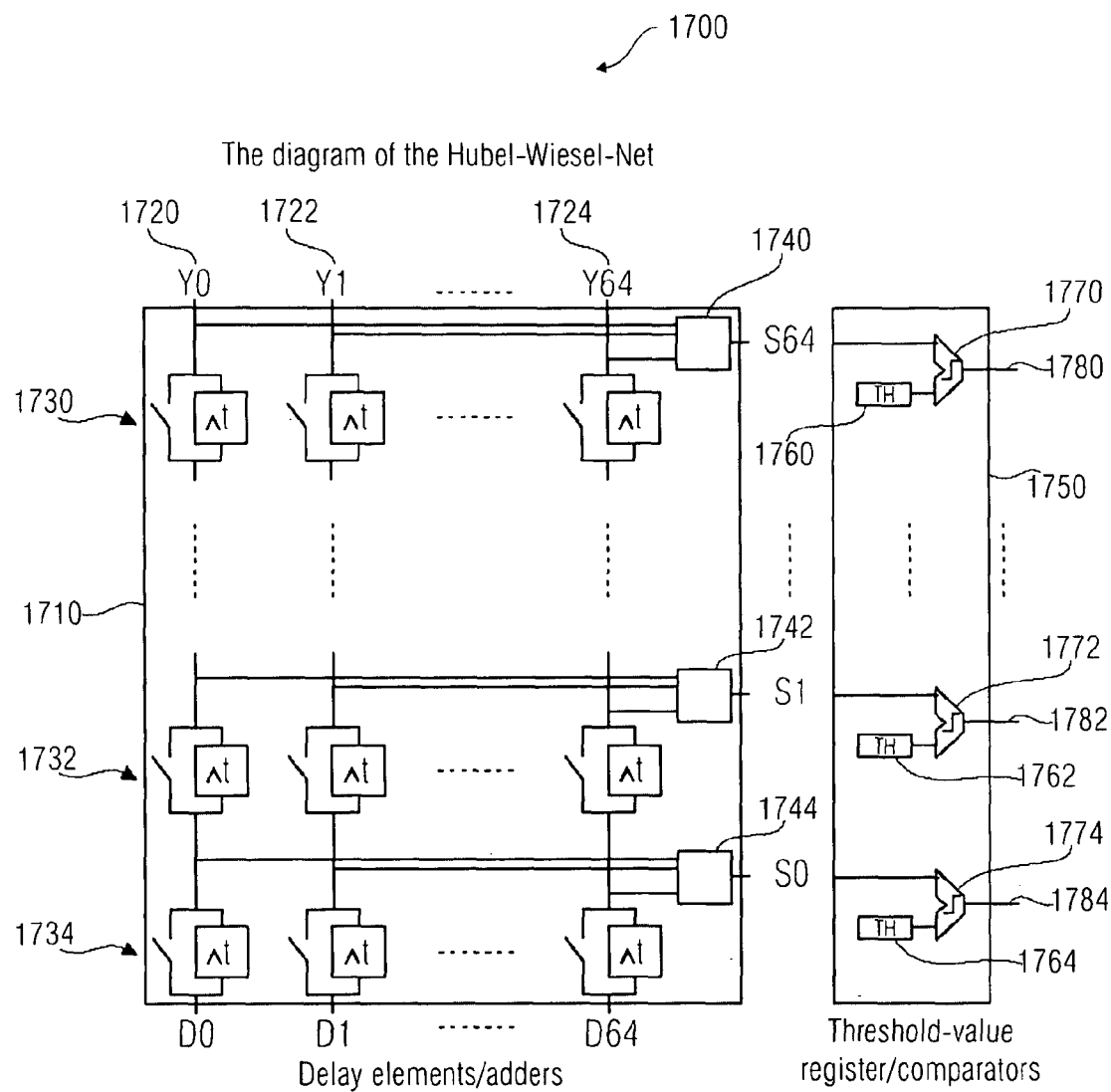
FIG. 17 is a circuit diagram of a Hubel-Wiesel net for performing, according to the invention, a pattern recognition.

FIG. 17 shows a diagram of an exemplary Hubel-Wiesel net for the inventive calculation of an analysis representation of an audio signal according to the second embodiment of the present invention. The diagram of FIG. 17 is in its entirety designated with 1700. A first circuit block 1710 receives input signals 1720, 1722, 1724, which may represent a nerve activity pattern or an excitation pattern of a basilar membrane, for example. The input signals 1720, 1722, 1724 are then directed through a plurality of stages 1730, 1732, 1734. An input signal 1720 therefore passes a plurality of stages 1730, 1732, 1734, wherein an input signal 1720 in a stage 1730, 1732, 1734 either passes a delay means or is directly forwarded to a subsequent stage. In other words, the delay means may be bridged.

In other words, each stage for each signal includes a switchable delay means, wherein the delay means may be switched into a signal path having an input signal passing therethrough or may be bridged. Signals at the inputs of each stage are tapped and fed to summers 1740, 1742, 1744, wherein the signals present at the respective inputs of a stage are summed up. The first circuit block 1710 therefore forms a grid of delay elements and adders connected in the manner shown.

The Hubel-Wiesel net 1700 further comprises threshold-value means 1750, wherein a value each from a threshold-value register 1760, 1762, 1764 as well as an output of a summer 1740, 1743, 1744 are fed to a comparator 1770, 1772, 1772. Output signals 1780, 1782, 1784 of the comparators 1770, 1772, 1774 provide information on whether a number of signals are simultaneously active at the inputs of a given stage 1730, 1732, 1734, wherein a minimum number, at which an active output signal 1780, 1782, 1784 is output, is determined by the threshold-value registers 1760, 1762, 1764. In other words, the comparators 1770, 1772, 1774 serve to ascertain, in connection with the summers 1740, 1742, 1744 and the threshold-value registers 1760, 1762, 1764, if (e.g. after passing how many of the stages 1730, 1732, 1734) a trajectory read in via the inputs 1720, 1722, 1724 of the first block 1710 is straightened out.

The delays of the individual stages 1730, 1732, 1734 may be appropriately given so as to enable a recognition of a as many trajectories (or trajectory shapes) as possible.

Figure 18:
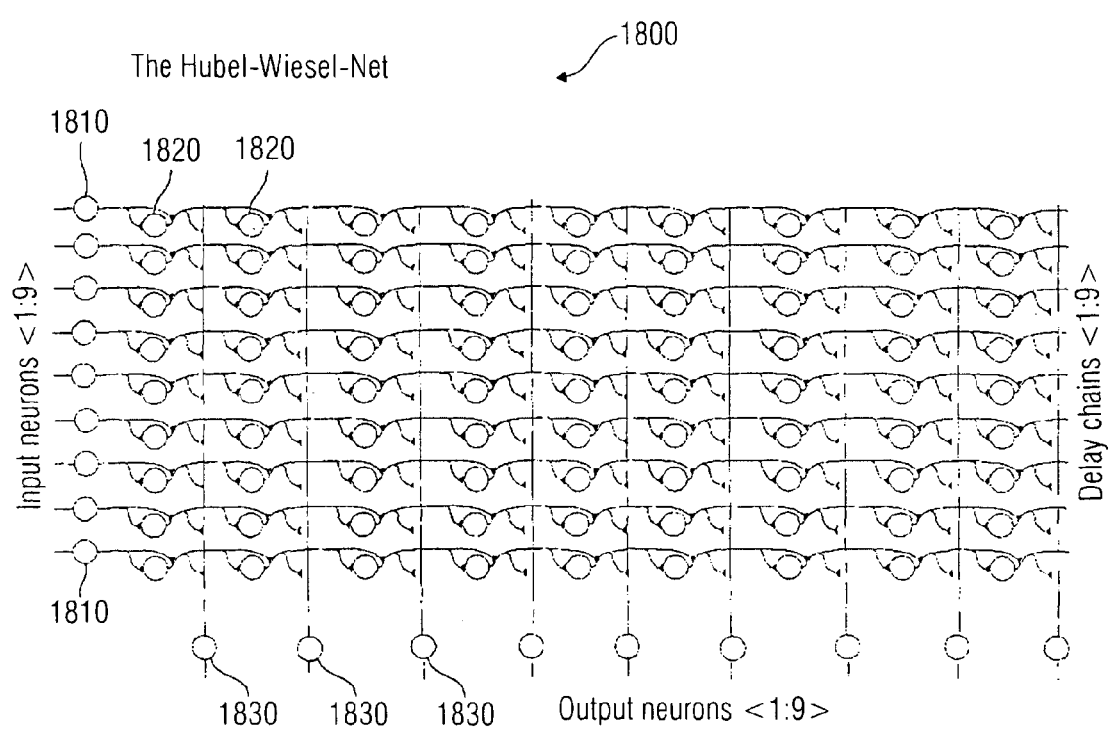
FIG. 18 is a circuit diagram of a Hubel-Wiesel net for performing, according to the invention, a pattern recognition, illustrated as a neuronal network.

FIG. 18 shows a block diagram of a Hubel-Wiesel net for the inventive identification of trajectories in an activity pattern according to the second embodiment of the present invention. The Hubel-Wiesel net shown is in its entirety designated with 1800.

Input neurons 1810 are configured to receive a nerve activity pattern, information on a neurotransmitter vesicle occurrence in a plurality of inner hair cells of an ear model, an excitation pattern of a basilar membrane of an ear model or another spatio-temporal activity pattern in an ear model in the form of parallely present time signals. The nerve activity pattern (and/or the excitation pattern of the basilar membrane) or another spatio-temporal activity pattern is forwarded through several stages of the neuronal net, optionally involving delay neurons. It is to be noted here that the delay neurons 1820 may also be bridged so that no delay of a signal supplied by an input neuron 1810 takes place in a stage. The neuronal net further comprises output neurons 1830. The connection of the neuronal net 1800 can be gathered from FIG. 18. It is to be noted that the neuronal net shown is capable of recognizing a curved graph or trajectory in a nerve activity pattern (and/or basilar-membrane excitation pattern) that is input to the neuronal net 1800 via the input neurons 1810. Here, the neuronal net is capable (after a training) of determining both the time and the shape of a trajectory in a nerve activity pattern input via the input neurons 1810, wherein an active output neuron describes this information. The information on the shape and time of a trajectory is encoded by the fact which output neuron is activated when.

Figure 19:
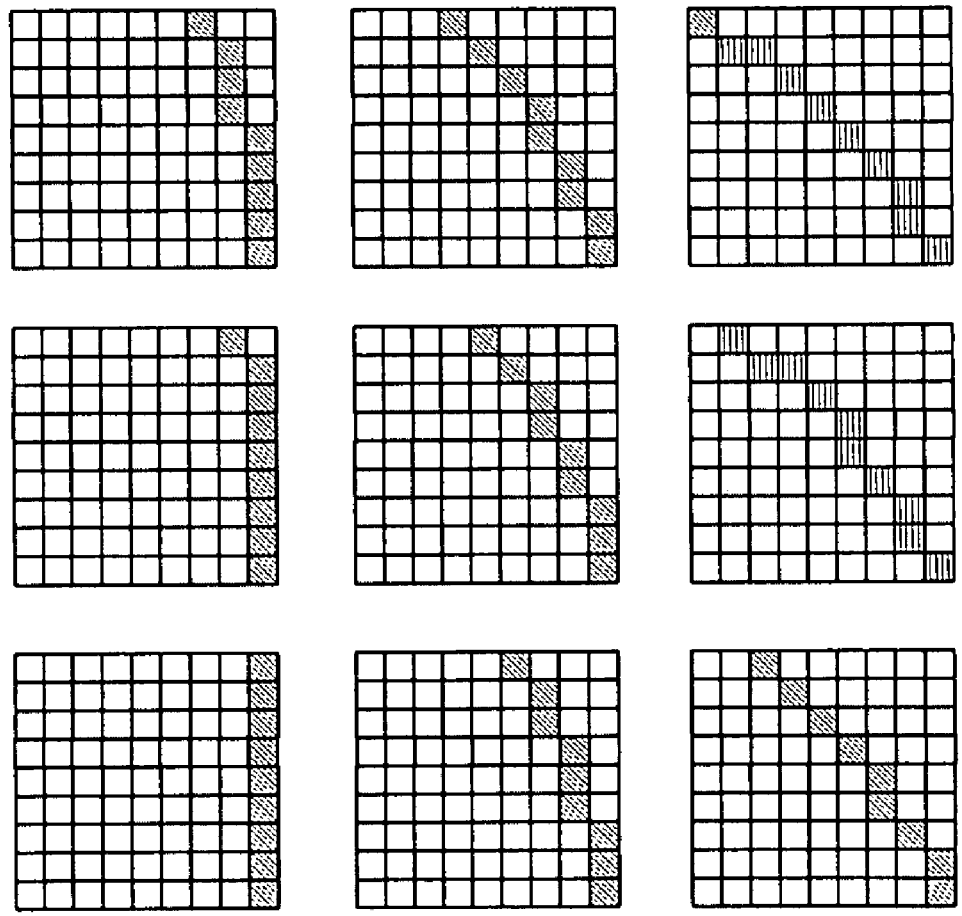
FIG. 19 is a graphic illustration of training patterns for training a Hubel-Wiesel net

Finally, FIG. 19 shows a graphic representation of exemplary separation patterns that may be used for training a neuronal net 1800. After a training, the neuronal net 1800 is then capable of identifying respective straight or curved courses as trajectories.

It is therefore to be stated that a Hubel-Wiesel net 1800 is very suitable for recognizing trajectories in a nerve activity pattern. For this purpose, one only applies the nerve activity pattern to inputs 1720, 1722, 1724 of the Hubel-Wiesel net. At outputs 1780, 1782, 1784 of comparators 1770, 1772, 1774 there will then be present signals that include a statement on the shape and temporal position of a trajectory. The output signal 1780, 1782, 1784 may naturally, if necessitated, be brought into a form that is easier to interpret and that e.g. a temporal information on a trajectory directly emerges from. Therefore, the information obtained may be used for determining, which activity events or activity impulses pertain to a trajectory and/or which activity events or activity impulses do not pertain to a trajectory.

It is furthermore to be noted that the processing of the nerve activity pattern (or, in general: the activity pattern) is advantageously effected by utilizing a so-called Hough transform (cf. U.S. Pat. No. 3,069,654). That is, a Hough transform is capable of effectively recognizing subsequent trajectories in a spatio-temporal pattern. For this reason, the Hough transform is excellently suited for recognizing trajectories in an activity pattern based on an audio signal.

It is furthermore to be noted that other known methods of pattern recognition may be used for recognizing trajectories in the nerve activity pattern. For example, what may be especially advantageously used is those methods enabling recognizing curved lines, as it has been discovered that trajectories in the nerve activity pattern or in any of the other activity patterns described typically exhibit a hyperbolic shape. It is to be taken into account here that the nerve activity pattern for a plurality of nerves over time yields a two-dimensional pattern, wherein, along a first direction, signals on several nerve fibers may be represented by an intensity distribution and/or by numerical values, for example, whereas, in a second direction, there is plotted a temporal development (or vice versa). A typical mode of representation of a temporal curve of a nerve activity pattern may therefore be similar to the cochlea diagrams (cochleagrams) shown, for example.

It is therefore possible to employ any pattern-recognition algorithm capable of recognizing curved lines. It shows, however, that the use of a Hough transform is particularly advantageous, as it is the Hough transform that is particularly well suited for a recognition of a curved lines. Beyond that, it is to be noted that, in performing a Hough transform in an arrangement 1700 and/or 1800, even if closely adjacent trajectories are present, a good recognition result may be achieved when the threshold values and/or response sensitivities of the output neurons (or of the comparators) only are appropriately set.

It is further possible to also recognize, in the context of a Hough transform (or another pattern recognition operation), a length of a trajectory so that, apart from information on the time and shape of the trajectory, there is also available a third information for the subsequent filtering out of activity events not contributing to an intelligibility of speech of a sound.

In addition, it is to be noted that a two-dimensional pattern comparison may also be performed over the temporal representation of the nerve activity pattern so as to obtain a series of time information describing temporal positions of subsequent trajectories.

Figure 20:
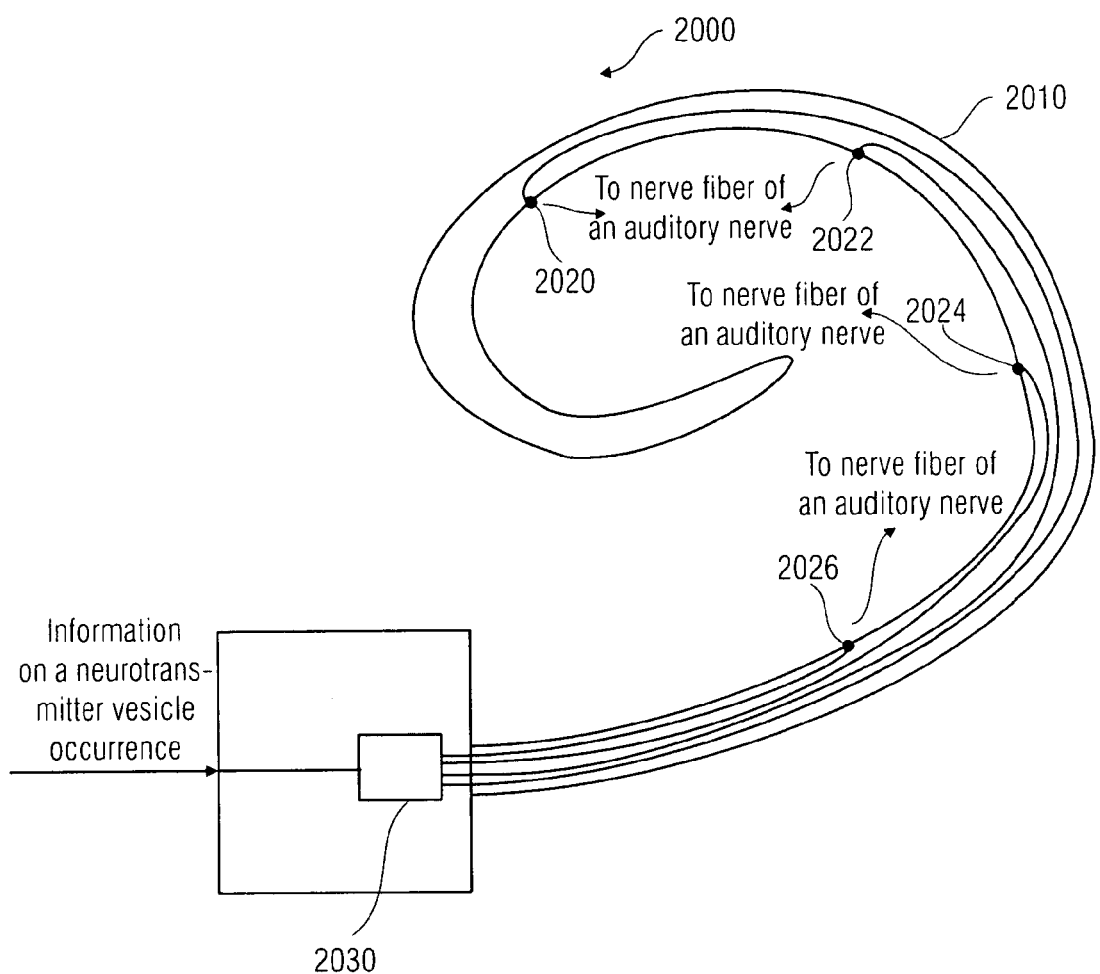
FIG. 20 is a schematic illustration of a cochlear implant for use in connection with the present invention.

FIG. 20 shows a schematic representation of a cochlear implant for use in connection with the present invention. The schematic representation of FIG. 20 is in its entirety designated with 2000. The cochlear implant shown in the schematic representation 2000 includes an electrode support 2010. The electrode support 2010 is configured for use in a human ear. The electrode support 2010 includes electrodes 2020, 2022, 2024, 2026 configured to excite several nerve fibers of a (human or animal) auditory nerve. In other words, the electrodes 2020, 2022, 2024, 2026 are configured to excite different auditory nerves pertaining two different inner hair cells disposed at different locations along the cochlea. The cochlear implant 2000 further includes electrode control means 2030 coupled to the electrodes 2020, 2022, 2024, 2026 and configured to impart a control signal, e.g. an electrical one, to the electrodes 2020, 2022, 2024, 2026. The electrode control means 2030 is otherwise configured to receive information on a neurotransmitter vesicle occurrence so as to generate, based on the neurotransmitter vesicle occurrence received, control signals for the excitation of different nerve fibers of the auditory nerve.

The electrode control means 2030 may, however, further be configured to receive another activity pattern occurring in an ear model, for example a nerve activity pattern of nerve fibers coupled to the plurality of inner hair cells of an auditory model. Apart from that, the cochlear implant 2000 may be configured for exciting the nerve fibers of the human or animal auditory nerve in different ways, for example electrically, chemically or mechanically. Generally put, one may say that the cochlear implant 2000 has the task of obtaining or receiving information on an activity pattern, which is cleared in the inventive manner, for example, and of exciting, based on the cleared information and the cleared activity pattern, nerve fibers of an auditory nerve.

Figure 21:
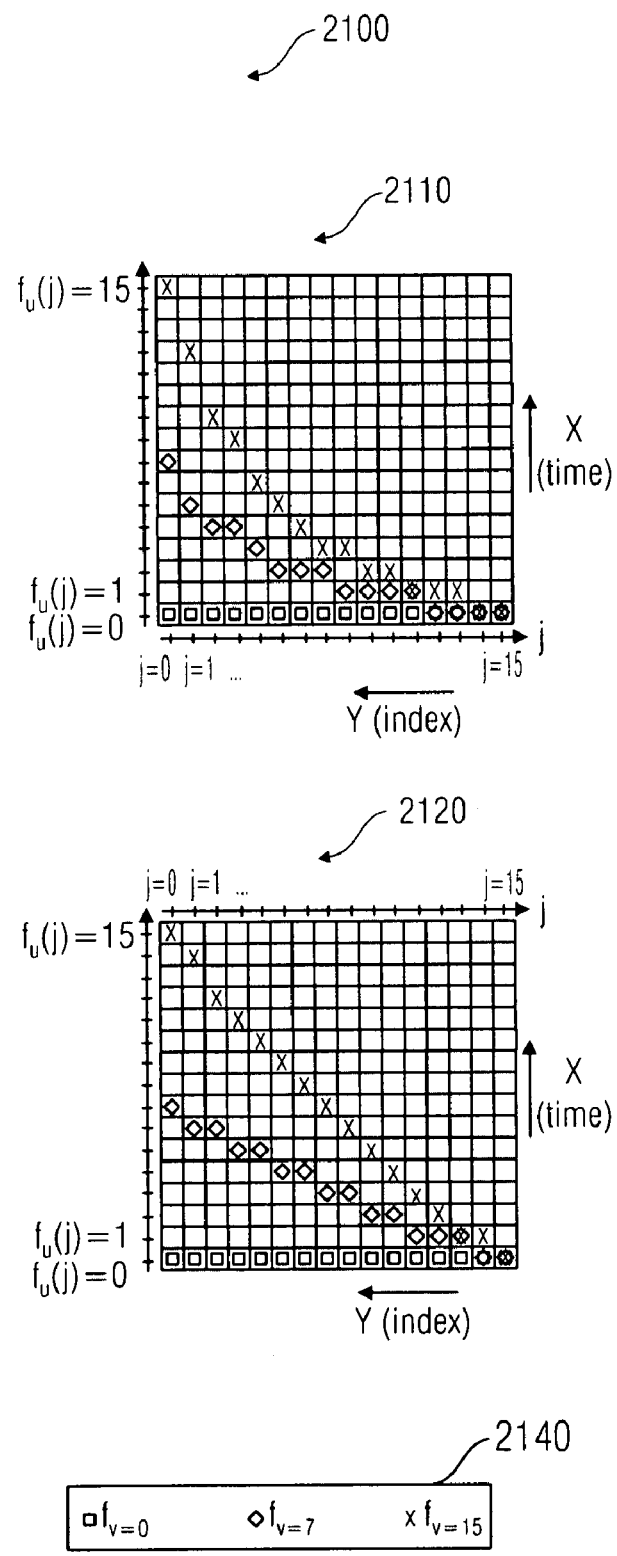
FIG. 21 shows graphic representations of possible trajectories having different curvatures.

FIG. 21 shows a graphic representation of possible trajectories that may be recognized in a two-dimensional representation of the activity pattern as described by means of FIGS. 13 and 14, for example, by an arrangement 1500, 1700 or 1800. The graphic representation of FIG. 21 is in its entirety designated with 2100. The possible trajectories are shown in the form of a pattern of pixels in the graphic representation of FIG. 21, wherein activity events are represented in a first direction x as a function of time, and wherein the activity events for different inner hair cells for different nerve fibers are represented in a second direction y.

The graphic representation 2100 of FIG. 21 shows two graphic representations 2010, 2020 describing trajectories having different curvatures. The positions of the activity impulses in the graphic representations 2010, 2020 are described for different curve indices $v$ ($v=1, \ldots, n_{p-1}$) and for different curvatures $f_{min}$ by the following context:

$$f_v(j) = \frac{f_{min} \cdot v \cdot (n_p - 1 - j)}{(j + f_{min}) \cdot (n_p - 1)}.$$

Here, $n_p$ is the size of a square graphic representation showing the respective trajectories. In other words, $n_p$ indicates the number of inner hair cells accounted for in a calculation of a trajectory. j is an index of the inner hair cells, which indicates, in which inner hair cell an activity event is to be calculated. $v$ is an index of the curve observed, wherein:

$v=0, 1, \ldots, n_{p-1}$

Furthermore:

$j=0, 1, \ldots, n_{p-1}$ $f_{min}$ is a free variable used for describing an average curvature of the trajectories.

$f_v$ (j) therefore describes the temporal position of an activity impulse in or at an inner hair cell having the index j. The running index $v$ serves to describe different trajectories of a group of possible trajectories.

For example, the graphic representations 2110, 2120 each show three trajectories of the exemplary group of e.g. 16 trajectories, that is the trajectories having the group indices $v=0$, $v=7$ and $v=15$ (cf. legend 2140).

The present invention is therefore based on an arrangement in which neurotransmitter vesicles are interpreted as electrical impulses in a 1:1 manner so that each neurotransmitter vesicle triggers an electrical impulse that is directed to the cochlear implant. Neurobiology teaches that a neurotransmitter vesicle may not trigger an action potential at downstream spiral ganglion cells unless the respective spiral ganglion cell is not in a refractory period. If briefly before, an earlier neurotransmitter vesicle generated an action potential (in the spiral ganglion cell), the refractory period determines the time until a new rest potential is reached. The triggering of action potentials may be modeled according to the so-called Hodgkin-Huxley equations, for example, which are described in the publication "Computing with Spiking Neurons" by W. Mass (In: Maass, W., Bishop, C. (Ed.): Pulsed Neuro Nets. Cambridge; MIT Press, 1998), on pp. 397-404. Further details may also be gathered from the previously mentioned publication "Schallanalyse: Neuronale Repräsentation des Hörvorgangs als Basis" (Analysis of sound: Neuronal Representation of the Auditory Process as a Basis) by G. Szepannek, F. Klefenz and C. Weihs.

Each action potential may be uniquely ascribed to and allocated to a triggering neurotransmitter vesicle. This is where a first back filtration starts. Only those neurotransmitter vesicles that generate an action potential are stored and selectively directed to the cochlear implant. In quasi stationary excitation sounds such as vocals, the neurotransmitter vesicle distribution consists of bundles of delay trajectories. The delay trajectories are detected according to time of occurrence and shape of curvature in a neuronal Hubel-Wiesel feed forward timing neural net. If the presence of a delay trajectory is ascertained, all neurotransmitter vesicles pertaining to the delay trajectory are marked. Same are selectively forwarded to the cochlear implant. The other neurotransmitter vesicles are canceled.

It is further to be noted that, in addition, it is, in a further embodiment, advantageous to suppress vesicles of the delay trajectories, that is filter out (eliminate) those vesicles that are part of delay trajectories and only forward to the cochlear implant the remaining vesicles that are not part of the delay trajectories. This serves to remove certain interfering events from the audio signal (such as e.g. "clicks"), for example, as same are characterized by a characteristic trajectory.

Apart from that, it has proven advantageous to perform, as an alternative, a filtering of the activity pattern over time in a plurality of e.g. n bands.

Furthermore, it has turned out that the recognition of trajectories as described with respect to FIGS. 15 to 19 may in a particularly advantageous manner be realized in an intellectual property core defined by the hardware description language VHDL. Such a realization is based on forming a Hubel-Wiesel net as shown with respect to FIGS. 17 and 18, for example, as a circuit implementation in the form of a clocked logic circuit.

The present invention therefore involves the advantage that the intelligibility of speech of an audio signal may be substantially increased for patients having a cochlear implant by, in the generation of control signals for a cochlear implant, filtering out of an activity pattern in or at inner hair cells of an auditory model those activity impulses that are not relevant for an intelligibility of speech.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

The invention claimed is:

1. A method of generating a control signal for a cochlear implant, based on an audio signal, comprising:
   calculating first information describing an activity pattern over time at a plurality of inner hair cells of an auditory model, which is yielded based on the audio signal;
   filtering out activity events described by the first information based on a recognition of a characteristic pattern in the activity pattern, for achieving, from the first information, cleared information by eliminating activity events pertaining to a characteristic pattern or by eliminating activity events not pertaining to a characteristic pattern,
   wherein the recognition of a characteristic pattern comprises recognizing a line-shaped curve in a representation of the activity pattern over time and over an index of the inner hair cells as a characteristic pattern; and
   using the cleared information as a control signal for a cochlear implant, or deriving a control signal for a cochlear implant from the cleared information.

2. The method of claim 1, wherein the method comprises transmitting the control signal to the cochlear implant.

3. The method of claim 1, wherein the method comprises imparting electrodes of the cochlear implant with the control signal.

4. The method of claim 1, wherein the first information describes, via the activity pattern, over time, temporal devolutions of a number of released neurotransmitter vesicles for a plurality of inner hair cells, and
   wherein the filtering out comprises removing neurotransmitter vesicle occurrences not contributing to a generation of an action potential or generating an action potential, from the first information.

5. The method of claim 4, wherein a removing of neurotransmitter vesicle occurrences comprises setting to zero a number of released neurotransmitter vesicles in a certain time interval for a certain hair cell, when neurotransmitter vesicles released in the certain hair cell in the certain time interval do not contribute to a generation of an action potential on a nerve fiber coupled to the certain hair cell or generate an action potential on the nerve fiber coupled to the certain hair cell.

6. The method of claim 4, wherein the filtering out comprises removing neurotransmitter vesicle occurrences for hair cells, which, due to a temporally previous release of an action potential are in a refractory period.

7. The method of claim 1, wherein the filtering out comprises determining, which of the activity events described by the first information do not pertain to a trajectory, and deriving the cleared information on the activity pattern, wherein the cleared information is derived from the first information by eliminating activity events not pertaining to a trajectory.

8. The method of claim 1, wherein the filtering out comprises determining, which of the activity events described by the first information pertain to a trajectory, and deriving the cleared information on the activity pattern, wherein the cleared information is derived from the first information by eliminating activity events pertaining to a trajectory.

9. The method of claim 7, wherein the first information describes temporal devolutions of a number of released neurotransmitter vesicles for a plurality of inner hair cells, wherein each inner hair cell of the plurality of inner hair cells has allocated thereto a temporal devolution.

10. The method of claim 7, wherein the first information describes a plurality of temporal voltage shapes at a plurality of nerve fibers coupled to different inner hair cells, wherein each inner hair cell of the plurality of inner hair cells has allocated thereto a temporal voltage shape on an associated nerve fiber.

11. The method of claim 7, wherein a trajectory describes an occurrence of activity events at a plurality of inner hair cells due to the same event in the audio signal.

12. The method of claim 7, wherein a certain trajectory includes of a plurality of activity events at a plurality of inner hair cells, and
   wherein the activity events pertaining to a trajectory approximate, in a two-dimensional graphic representation (a straight or curved line,
   wherein, in the two-dimensional graphic representation, the time is plotted on a first axis, and wherein an index of the hair cells the temporal devolutions pertain to is plotted on a second axis and,
   wherein the activity events are identified in the two-dimensional representation.

13. The method of claim 7, wherein the determining, which of the activity events described by the first information pertain to a trajectory or do not pertain to a trajectory, comprises performing a pattern recognition, wherein the performing of the pattern recognition comprises:
   receiving the first information on the activity pattern over time;
   interpreting the activity pattern over time for a plurality of hair cells as a two-dimensional representation, wherein a first direction of the two-dimensional representation describes the time, wherein a second direction of the two-dimensional representation describes an index of the hair cells, and wherein the information included in the two-dimensional representation describes an occurrence of activity events as a function of the time and of the index of the inner hair cells; and
   identifying a curve shape in the two-dimensional representation as a trajectory, if the curve shape exhibits, with respect to a given measure of similarity, at least one given similarity to a comparative curve shape.

14. The method of claim 13, wherein the performing of the pattern recognition comprises:
   receiving information from the first information on activity events at different inner hair cells at a first time or for a first time interval;
   interpreting the information for the first time or for the first time interval as a first row of a two-dimensional representation of a first information;
   receiving information from the first information on activity events at different inner hair cells for a second time or for a second time interval; and
   interpreting the information for the second time or for the second time interval as a second row of a two-dimensional representation of the first information.

15. The method of claim 13, wherein the identifying of a curve shape in the two-dimensional representation comprises comparing the two-dimensional representation or a cut-out of the two-dimensional representation to a comparative pattern.

16. The method of claim 13, wherein the identifying of a curve shape in the two-dimensional representation comprises identifying a straight or hyperbolically curved curve shape.

17. The method of claim 13, wherein the comparative curve shape is a straight or hyperbolic curve.

18. The method of claim 13, wherein the identifying of a curve shape in the two-dimensional representation as a trajectory comprises a step-by-step distorting of the two-dimensional representation so as to achieve a distorted two-dimensional representation of the activity pattern over time, as well as determining if an approximately straight line is included in the distorted two-dimensional representation,
   wherein an approximately straight line recognized in the distorted two-dimensional representation is identified as a trajectory.

19. The method of claim 18, wherein the step-by-step distorting takes place such that a curved line included in the two-dimensional representation is straightened out in a step-by-step manner by the step-by-step distorting.

20. The method of claim 13, wherein the identifying of a curve shape in the two-dimensional representation as a trajectory comprises applying a Hough transform, which is configured for a recognition of straight or curved graph segments, to the two-dimensional representation, wherein a trajectory is recognized based on a result of the Hough transform.

21. The method of claim 13, wherein the identifying of a curve shape in the two-dimensional representation as a trajectory comprises inputting the two-dimensional representation to a neuronal net, wherein the neuronal net is configured to recognize a curve shape forming a trajectory in the two-dimensional representation.

22. The method of claim 7, wherein the determining, which activity events pertain or do not pertain to a trajectory, comprises determining activity events pertaining to a trajectory,
   wherein a trajectory is not recognized unless a number of activity events pertaining together and caused by the same event in the audio signal are larger than a given minimum number.

23. The method of claim 22, wherein an event in the audio signal comprises an onset of a vocal, of a consonant, of a sound or of a click.

24. The method of claim 7, wherein a trajectory is formed by a plurality of activity impulses at a plurality of inner hair cells describing a traveling wave on a basilar membrane of the ear model.

25. The method of claim 7, wherein a trajectory comprises activity events at a plurality of inner hair cells, which are triggered by an excitation of the plurality of inner hair cells by a single traveling wave on a basilar membrane of the ear model.

26. The method of claim 7, wherein the deriving of the cleared information comprises recognizing a trajectory in the first information, marking activity events pertaining to the trajectory as well as eliminating unmarked activity events.

27. The method of claim 26, wherein the deriving of the cleared information comprises marking activity events, the distance of which from a trajectory recognized is less than a given maximum distance.

28. The method of claim 1, wherein the calculating of the first information on the activity pattern over time comprises calculating the activity pattern over time at a plurality of inner hair cells of an auditory model, wherein the inner hair cells are arranged at different locations along the cochlea.

29. The method of claim 1, wherein the inner hair cells exhibit sensitivity peaks at different frequencies included in the audio signal.

30. The method of claim 1, wherein the cleared information is cleared information on a neurotransmitter vesicle occurrence, and wherein the using of the cleared information comprises transferring the cleared information to the cochlear implant.

31. The method of claim 1, wherein the cleared information is a cleared nerve activity pattern, and wherein the using of the cleared information comprises transferring the cleared information to the cochlear implant.

32. A tangible computer readable medium storing a computer program for performing, when the computer program runs on a computer, a method of generating a control signal for a cochlear implant, based on an audio signal, comprising:
   calculating first information describing an activity pattern over time at a plurality of inner hair cells of an auditory model, which is yielded based on the audio signal;
   filtering out activity events described by the first information based on a recognition of a characteristic pattern in the activity pattern, for achieving, from the first information, cleared information by eliminating activity events pertaining to a characteristic pattern or by eliminating activity events not pertaining to a characteristic pattern,
   wherein the recognition of a characteristic pattern comprises recognizing a line-shaped curve in a representation of the activity pattern over time and over an index of the inner hair cells as a characteristic pattern; and using the cleared information as a control signal for a cochlear implant, or deriving a control signal for a cochlear implant from the cleared information.

33. A device for generating a control signal for a cochlear implant based on an audio signal, comprising:
- a calculator for calculating a first information on an activity pattern over time at a plurality of inner hair cells of an auditory model, which is yielded due to the audio signal;
- a filter for filtering out activity events described by the first information based on a recognition of a characteristic pattern in the activity pattern in order to achieve, from the first information, cleared information, by eliminating activity events pertaining to a characteristic pattern, or by eliminating activity events not pertaining to a characteristic pattern,
- wherein the recognition of a characteristic pattern comprises recognizing a line-shaped curve in a representation of the activity pattern over time and over an index of the inner hair cells as a characteristic pattern; and
- a controller for controlling the cochlear implant, which is configured to use the cleared information or information derived from the cleared information as a control signal for the cochlear implant.

34. The device of claim 33, wherein the controller for controlling the cochlear implant is configured to transmit the control signal to the cochlear implant.

35. The device of claim 33, wherein the controller for controlling the cochlear implant is configured to impart electrodes of the cochlear implant with the control signal.

36. The device of claim 33, comprising:
- a determiner for determining, which of the activity events described by the first information, do not pertain to a trajectory, and
- a deriver for deriving the cleared information on the activity pattern by eliminating activity events not pertaining to a trajectory, on the first information.

37. The device of claim 33, wherein the first information describes temporal devolutions of a number of released neurotransmitter vesicles for a plurality of inner hair cells, wherein each inner hair cell of the plurality of inner hair cells has allocated thereto a temporal devolution.

38. The device of claim 33, wherein the first information describes a plurality of temporal voltage shapes at a plurality of nerve fibers coupled to different inner hair cells, wherein each inner hair cell of the plurality of inner hair cells has allocated thereto a temporal voltage shape on an associated nerve fiber.

39. The device of claim 33, wherein the deriver for determining, which of the activity events described by the first information do not pertain to a trajectory, comprise a curve recognizer configured to receive the activity pattern over time at the plurality of hair cells in the form of parallel signals in a parallel manner, wherein each signal is allocated to a hair cell, and to forward the signals through a plurality of stages connected one after the other at different speeds,
- wherein at least one predetermined stage of the plurality of stages connected one after the other comprises a threshold-value recognizer configured to recognize, when at least a given number of signals are simultaneously active in the predetermined stage,
- wherein the presence of at least the given number of simultaneously active signals in the predetermined stage indicates a presence of a trajectory in the activity pattern.

40. The device of claim 39, wherein at least one stage is configured to delay multiple signals more or less in a forwarding through the stage.

41. The device of claim 33, wherein the filter for filtering out comprises a performer for performing a parallel Hough transform, which is configured to indicate the presence of a trajectory in the activity pattern, wherein a trajectory forms a characteristic pattern in the activity pattern.

* * * * *